US012173081B2

(12) United States Patent
Presta et al.

(10) Patent No.: US 12,173,081 B2
(45) Date of Patent: Dec. 24, 2024

(54) CD19/CD38 MULTISPECIFIC ANTIBODIES

(71) Applicant: Biograph 55, Inc., San Francisco, CA (US)

(72) Inventors: Leonard Presta, San Francisco, CA (US); Paul Tumeh, San Francisco, CA (US); Nils Lonberg, Woodside, CA (US)

(73) Assignee: Biograph 55, Inc., San Francisco, CA (US)

( * ) Notice: Subject to any disclaimer, the term of this patent is extended or adjusted under 35 U.S.C. 154(b) by 0 days.

(21) Appl. No.: 18/612,854

(22) Filed: Mar. 21, 2024

(65) Prior Publication Data

US 2024/0317883 A1    Sep. 26, 2024

Related U.S. Application Data

(60) Provisional application No. 63/491,441, filed on Mar. 21, 2023, provisional application No. 63/590,886, filed on Oct. 17, 2023.

(51) Int. Cl.
C07K 16/28 (2006.01)
A61P 35/00 (2006.01)
A61K 39/00 (2006.01)

(52) U.S. Cl.
CPC .......... *C07K 16/2896* (2013.01); *A61P 35/00* (2018.01); *C07K 16/2803* (2013.01); *A61K 39/00* (2013.01); *C07K 2317/31* (2013.01)

(58) Field of Classification Search
CPC ............ C07K 16/2896; C07K 2317/31; C07K 2317/565
USPC .................................................... 424/136.1
See application file for complete search history.

(56) References Cited

U.S. PATENT DOCUMENTS

| | | |
|---|---|---|
| 5,500,362 A | 3/1996 | Robinson et al. |
| 5,624,821 A | 4/1997 | Winter et al. |
| 5,648,260 A | 7/1997 | Winter et al. |
| 5,821,337 A | 10/1998 | Carter et al. |
| 6,602,684 B1 | 8/2003 | Umana et al. |
| 7,276,241 B2 | 10/2007 | Schneider et al. |
| 7,371,826 B2 | 5/2008 | Presta |
| 7,553,930 B2 | 6/2009 | Desjarlais et al. |
| 7,635,767 B2 | 12/2009 | Rixon et al. |
| 7,691,804 B2 | 4/2010 | Jeffrey et al. |
| 7,709,220 B2 | 5/2010 | Ambrose et al. |
| 7,943,743 B2 | 5/2011 | Korman et al. |
| 7,947,805 B2 | 5/2011 | Belloir et al. |
| 8,008,449 B2 | 8/2011 | Korman et al. |
| 8,097,703 B2 | 1/2012 | Rao-Naik et al. |
| 8,106,163 B2 | 1/2012 | Heusser et al. |
| 8,193,316 B2 | 6/2012 | Fang et al. |
| 8,258,268 B2 | 9/2012 | Wu et al. |
| 8,263,746 B2 | 9/2012 | Tesar et al. |
| 8,354,509 B2 | 1/2013 | Carven et al. |
| 8,409,577 B2 | 4/2013 | Thompson et al. |
| 8,609,821 B2 | 12/2013 | Huard et al. |
| 8,642,745 B2 | 2/2014 | Arathoon et al. |
| 9,040,050 B2 | 5/2015 | Van De Winkel et al. |
| 9,056,917 B2 | 6/2015 | Hansen et al. |
| 9,097,726 B2 | 8/2015 | Hsu et al. |
| 9,150,664 B2 | 10/2015 | Kufer et al. |
| 9,200,061 B2 | 12/2015 | Tesar et al. |
| 9,243,058 B2 | 1/2016 | Armitage et al. |
| 9,249,226 B2 | 2/2016 | De Weers et al. |
| 9,290,582 B2 | 3/2016 | Yang et al. |
| 9,359,448 B2 | 6/2016 | Allan et al. |
| 9,458,246 B2 | 10/2016 | Hsu et al. |
| 9,603,927 B2 | 3/2017 | Doshi |
| 9,758,590 B2 | 9/2017 | Tesar et al. |
| 9,840,543 B2 | 12/2017 | Brodeur et al. |
| 9,932,412 B2 | 4/2018 | Kim et al. |
| 9,944,711 B2 | 4/2018 | De Weers et al. |
| 9,969,808 B2 | 5/2018 | Van et al. |
| 9,988,452 B2 | 6/2018 | Freeman et al. |
| 10,072,088 B2 | 9/2018 | Pillarisetti et al. |
| 10,144,782 B2 | 12/2018 | Oden et al. |
| 10,266,608 B2 | 4/2019 | Wu |

(Continued)

FOREIGN PATENT DOCUMENTS

| | | |
|---|---|---|
| AU | 2015228454 A1 | 8/2016 |
| AU | 2015366213 A1 | 6/2017 |

(Continued)

OTHER PUBLICATIONS

Voskoglou-Nomikos (Clin. Can. Res. 9:4227-4239 (2003)).*

(Continued)

*Primary Examiner* — Lynn A Bristol
(74) *Attorney, Agent, or Firm* — Wilson Sonsini Goodrich & Rosati

(57) ABSTRACT

Provided herein are common light chain bispecific antibodies that bind CD38 and CD19. The common light chain bispecific antibodies comprise an anti-CD38 heavy chain variable region and anti CD19 heavy chain variable region that each have a negatively-charged amino acid at a terminal heavy chain variable region position. The common light chain bispecific antibodies comprise further comprise an anti-CD38 heavy chain constant region and anti-CD19 heavy chain constant region that each lack a C-terminal lysine residue. Further provided are nucleic acids encoding such common light chain bispecific antibodies and host cells comprising the nucleic acids. Also provided are methods of making such common light chain bispecific antibodies.

13 Claims, 5 Drawing Sheets
Specification includes a Sequence Listing.

(56) References Cited

U.S. PATENT DOCUMENTS

| | | |
|---|---|---|
| 10,519,251 B2 | 12/2019 | Wu |
| 10,711,063 B2 | 7/2020 | Andre et al. |
| 11,299,551 B2 | 4/2022 | Presta et al. |
| 2005/0014934 A1 | 1/2005 | Hinton et al. |
| 2005/0112596 A1 | 5/2005 | Tschopp et al. |
| 2005/0130892 A1 | 6/2005 | Desjarlais et al. |
| 2006/0240520 A1 | 10/2006 | Ambrose et al. |
| 2009/0055944 A1 | 2/2009 | Korman et al. |
| 2009/0123950 A1 | 5/2009 | Tesar |
| 2009/0217401 A1 | 8/2009 | Korman et al. |
| 2010/0203056 A1 | 8/2010 | Irving et al. |
| 2011/0008369 A1 | 1/2011 | Finnefrock et al. |
| 2011/0117085 A1 | 5/2011 | Rotem-Yehudar et al. |
| 2011/0223188 A1 | 9/2011 | Langermann |
| 2012/0039906 A1 | 2/2012 | Olive |
| 2013/0017199 A1 | 1/2013 | Langermann |
| 2013/0071403 A1 | 3/2013 | Rolland et al. |
| 2013/0095097 A1 | 4/2013 | Blankenship et al. |
| 2014/0024055 A1 | 1/2014 | Takeuchi et al. |
| 2014/0099254 A1 | 4/2014 | Chang et al. |
| 2014/0248211 A1 | 9/2014 | Bender |
| 2014/0322756 A1 | 10/2014 | Arathoon et al. |
| 2015/0017164 A1 | 1/2015 | Ponce, Jr. et al. |
| 2015/0125463 A1 | 5/2015 | Cogswell et al. |
| 2015/0218267 A1 | 8/2015 | Brodeur et al. |
| 2015/0284467 A1 | 10/2015 | Lipp et al. |
| 2015/0353637 A1 | 12/2015 | Wang et al. |
| 2016/0024225 A1 | 1/2016 | Hsu et al. |
| 2016/0096901 A1 | 4/2016 | Tesar et al. |
| 2016/0108123 A1 | 4/2016 | Freeman et al. |
| 2016/0123964 A1 | 5/2016 | Tumeh et al. |
| 2016/0176962 A1 | 6/2016 | Murriel et al. |
| 2016/0297884 A1 | 10/2016 | Kuo et al. |
| 2017/0095555 A1 | 4/2017 | Blake-Haskins et al. |
| 2017/0174780 A1 | 6/2017 | Doshi |
| 2017/0183418 A1 | 6/2017 | Galletto et al. |
| 2017/0209574 A1 | 7/2017 | Cao et al. |
| 2017/0320967 A1 | 11/2017 | Yang et al. |
| 2017/0369582 A1 | 12/2017 | Huard et al. |
| 2018/0179290 A1 | 6/2018 | Cosenza et al. |
| 2018/0194861 A1 | 7/2018 | Dong et al. |
| 2018/0222991 A1 | 8/2018 | Vu et al. |
| 2018/0273605 A1 | 9/2018 | Browning et al. |
| 2019/0038671 A1 | 2/2019 | Fan et al. |
| 2019/0135923 A1 | 5/2019 | Tumeh et al. |
| 2019/0177439 A1 | 6/2019 | Wu |
| 2020/0385478 A1 | 12/2020 | Tumeh |
| 2022/0185906 A1 | 6/2022 | Presta et al. |
| 2022/0185907 A1 | 6/2022 | Presta et al. |
| 2022/0185908 A1 | 6/2022 | Presta et al. |
| 2022/0363774 A2 | 11/2022 | Presta et al. |

FOREIGN PATENT DOCUMENTS

| | | |
|---|---|---|
| AU | 2019300223 A1 | 1/2021 |
| AU | 2019370339 A1 | 6/2021 |
| AU | 2021226582 A1 | 10/2022 |
| EP | 1259544 B1 | 8/2011 |
| EP | 3103476 A2 | 12/2016 |
| WO | WO-9429351 A2 | 12/1994 |
| WO | WO-2004074511 A1 | 9/2004 |
| WO | WO-2007002223 A2 | 1/2007 |
| WO | WO-2007044616 A2 | 4/2007 |
| WO | WO-2008077546 A1 | 7/2008 |
| WO | WO-2009054863 A2 | 4/2009 |
| WO | WO-2009089004 A1 | 7/2009 |
| WO | WO-2012038068 A2 | 3/2012 |
| WO | WO-2012038068 A3 | 5/2012 |
| WO | WO-2012/038068 A8 | 11/2013 |
| WO | WO-2013186374 A1 | 12/2013 |
| WO | WO-2014145806 A2 | 9/2014 |
| WO | WO-2014191113 A1 | 12/2014 |
| WO | WO-2016/015095 A1 | 2/2016 |
| WO | WO-2016039801 A1 | 3/2016 |
| WO | WO-2016061142 A1 | 4/2016 |
| WO | WO-2016073760 A1 | 5/2016 |
| WO | WO-2016081746 A2 | 5/2016 |
| WO | WO-2016120810 A1 | 8/2016 |
| WO | WO-2017075477 A1 | 5/2017 |
| WO | WO-2017130223 A2 | 8/2017 |
| WO | WO-2017214170 A2 | 12/2017 |
| WO | WO-2018009904 A2 | 1/2018 |
| WO | WO-2018085690 A1 | 5/2018 |
| WO | WO-2018119215 A1 | 6/2018 |
| WO | WO-2019136311 | 7/2019 |
| WO | WO-2019195535 A1 | 10/2019 |
| WO | WO-2019197979 A1 | 10/2019 |
| WO | WO-2020180398 A1 | 9/2020 |
| WO | WO-2020210670 A1 | 10/2020 |
| WO | WO-2021146464 A1 | 7/2021 |
| WO | WO-2021173844 A1 | 9/2021 |
| WO | WO-2022032022 A2 | 2/2022 |
| WO | WO-2023028159 A1 | 3/2023 |
| WO | WO-2023028162 A1 | 3/2023 |
| WO | WO-2024042250 A1 | 2/2024 |

OTHER PUBLICATIONS

Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60: 1421-1434 (2008)).*
Rudnick et al. (Can. Biotherp. & Radiopharm. 24: 155-162 (2009)).*
Huang et al. (Appl Microbiol Biotechnol (2010) 87:401-410).*
Al-Lazikani et al.: Standard Conformations For The Canonical Structures Of Immunoglobulins. Journal of Molecular Biology 273(4):927-948 (1997).
Altschul et al.: Gapped BLAST and PSI-BLAST: A New Generation Of Protein Database Search Programs. Nucleic Acids Research. 25(17):3389-3402 (1997).
ATCC Raji data sheet; pp. 1-10 (2021).
Bae et al.: Pembrolizumab (anti-PD-1) Treatment Increases Anti-Tumor Activities of XBP1/CD138/CS1-Specific Cytotoxic T Lymphocytes Against Multiple Myeloma. Blood. American Society of Hematology. 130:1867 (2017).
Bald, et al. Immune Cell—Poor Melanomas Benefit from PD-1 Blockade after Targeted Type I IFN Activation. Cancer Discovery, 2014; 4:674-687.
Barthelemy, et al. Comprehensive Analysis of the Factor Contributing to the Stability and Solubility of Autonomous Human VH Domains. The Journal of Biological Chemistry, 283(6):3639-3654 (Feb. 8, 2008).
Beiboer, Sigrid H. et al. Guided Selection of a Pan Carcinoma Specific Antibody Reveals Similar Binding Characteristics yet Structural Divergence Between the Original Murine Antibody and its Human Equivalent. J. Mol. Biol. 296:833-849 (2000).
Berge et al., Pharmaceutical Salts. Journal of Pharmaceutical Sciences 66(1):1-19 (1977).
Brinkmann et al.: The making of bispecific antibodies. Mabs. 9(2):182-212 (2017).
Casset et al., A Peptide Mimetic Of An Anti-CD4 Monoclonal Antibody By Rational Design. Biochemical and Biophysical Research Communication 307:198-205 (2003).
Chang, Lung-Ji, Combination CAR-T Cell Therapy Targeting Hematological Malignancies. Clinical Trials NCT03125577; https://clinicaltrials.gov/ct2/show/NCT03125577 (2017).
Chen et al.: Selection And Analysis Of An Optimized Anti-VEGF Antibody: Crystal Structure Of An Affinity-matured Fab In Complex With Antigen. Journal of Molecular Biology 293(4):865-881 (1999).
Chinese Patent Application No. 201580072313.0 Office Action dated May 7, 2021.
Choi, Yoonjoo et al. Predicting antibody complementarity determining region structures without classification. Mol. BioSyst. 7:3327-3334 (2011).

(56) References Cited

OTHER PUBLICATIONS

Schwartz et al.: B cell regulation of the anti-tumor response and role in carcinogenesis. J Immunother Cancer. Jul. 19, 2016;4:40. doi: 10.1186/s40425-016-0145-x. eCollection 2016.
Clarkson et al.: Making Antibody Fragments Using Phage Display Libraries. Nature 352(6336):624-628 (1991).
International Search Report dated Feb. 15, 2016, from co-pending International Application PCT/US2015/059299 filed Nov. 5, 2015.
De Genst et al. Antibody repertoire development in camelids. Dev Comp Immunol 30(1-2):187-198 (2006).
De Pascalis, Roberto, et al., Grafting of "Abbreviated" Complementarity-Determining Regions Containing Specificity-Determining Residues Essential for Ligand Contact to Engineer a Less Immunogenic Humanized Monoclonal Antibody. The Journal of Immunology 169(6):3076-3084 (2002).
Denkert et al., Tumor-associated lymphocytes as an independent predictor of response to neoadjuvant chemotherapy in breast cancer, J Clin Oncol., 28(1): 105-113 (2010).
Deyoung, Joyce L, et al., Development of pancreatic enzyme microsphere technology and US findings with Pancrease in the treatment of chronic pancreatitis. The International Journal of Pancreatology 5:31-36 (1989).
Edelman et al.: The covalent structure of an entire yGim-munoglobulin molecule. PNAS 63(1):78-85 (1969).
Eissler et al.: Abstract 3812: A best in class anti-CD38 antibody with antitumor and immune-modulatory properties. DOI: 10.1158/1538-7445.AM2018-3812 Published Jul. 2018 (https://cancerres.aacrjournals.org/content/78/13_Supplement/3812 ).
European Patent Application No. 19736092.8 European Search Report dated Aug. 25, 2021.
Extended European Search Report dated Mar. 6, 2018 from corresponding European Application No. 15857303.0 (Publication No. EP3215852).
Fremd et al., B cell-regulated immune responses in tumor models and cancer patients, OncoImmunology, 2(7): e25443-1-e25443-9 (2013).
Gajewski et al. Cancer immunotherapy strategies based on overcoming barriers within the tumor microenvironment. Curr Opin Immunol 25:268-276 (2013).
Galon, et al. Towards the introduction of the 'Immunoscore' in the classification of malignant tumours. J Pathol. Jan. 2014;232(2):199-209. doi: 10.1002/path.4287.
Galon et al. Type, density, and location of immune cells within human colorectal tumors predict clinical outcome. Science 313:1960-1964 (2006).
Gentles et al., The prognostic landscape of genes and infiltrating immune cells across human cancers. Nat Med 21(8):938-945 (2015).
Griffiths et al.: Human anti-self antibodies with high specificity from phage display libraries. EMBO J. 12(2):725-734 (1993).
Halama, et al. The localization and density of immune cells in primary tumors of human metastatic colorectal cancer shows an association with response to chemotherapy. Cancer Immunity, Feb. 19, 2009, vol. 9, p. 1-6.
Hamid, et al. Safety and Tumor Responses with Lambrolizumab (Anti-PD-1) in Melanoma. N Engl J Med. Jul. 11, 2013; 369(2):134-144.
Hanahan, et al. Hallmarks of cancer: the next generation. Cell. Mar. 4, 2011. 144(5):646-74. doi: 10.1016/j.cell.2011.02.013.
Harris et al., Tumour cell killing using chemically engineered antibody constructs specific for tumour cells and the complement inhibitor CD59. Clin Exp Immunol 107(2):364-371 (1997).
Herbst, Roy S, et al., Predictive Correlates Of Response To The Anti-PD-L1 Antibody MPDL3280A In Cancer Patients. Nature 515(7528):563-567 (2014).
Holm et al. Functional mapping and single chain construction of the anti-cytokeratin 8 monoclonal antibody TS1. Mol Immunol 44(6):1075-1084 (2007).
Honegger et al.: Yet Another Numbering Scheme for Immunoglobulin Variable Domains: An Automatic Modeling and Analysis Tool. Journal of Molecular Biology 309(3):657-670 (2001).

Kabat et al.: Sequences of Proteins of Immunological Interest, 5th Ed. 5th Edition—US Department of Health and Human Services, NIH publication nº 91-3242 (1991).
Kabat et al.: Sequences of Proteins of Immunological Interest, NIH Publication No. 91-3242. U.S. Department of Health and Human Services, Public Health Service, National Institutes of Health 1:647-669 (1991).
Karlin et al.: Applications and Statistics for Multiple High-Scoring Segments in Molecular Sequences. Proceedings of the National Academy of Sciences of the United States of America 90(12):5873-5877 (1993).
Kindt et al., Kuby Immunology, Sixth Edition., W.H. Freeman and Co., p. 91 (2007).
Klein, Christian, et al., Progress in Overcoming the Chain Association Issue in Bispecific Heterodimeric IgG Antibodies. mAbs 4(6):653-663 (2012).
Klimka, A. et al. Human anti-CD30 recombinant antibodies by guided phage antibody selection using cell panning. British Journal of Cancer 83(2):252-260 (2000).
Krishnamurthy et al., Bispecific antibodies for cancer therapy: a review. Pharmacol Ther. 185:122-134 (2018).
Kroeger et al., Tumor-Infiltrating Plasma Cells Are Associated with Tertiary Lymphoid Structures, Cytolytic T-Cell Responses, and Superior Prognosis in Ovarian Cancer, Clin Cancer Res., 22(12): 3005-3015 (2016).
Lefranc et al.: IMGT Unique Numbering for Immunoglobulin and T Cell Receptor Variable Domains And Ig Superfamily V-like Domains. Developmental & Comparative Immunology 27(1):55-77 (2003).
Li et al. Cell culture processes for monoclonal antibody production. Mabs. 2(5):466-477 (2010).
Maccallum et al.: Antibody-Antigen Interactions: Contact Analysis and Binding Site Topography. Journal of Molecular Biology 262(5):732-745 (1996).
Malia et al., Epitope mapping and structural basis for the recognition of phosphorylated tau by the anti-tau antibody AT8. Proteins 84(4):427-434 (2016).
Mihara et al., T cells bearing anti-CD19 and/or anti-CD38 chimeric antigen receptors effectively abrogate primary double-hit lymphoma cells. J Hematol Oncol. 10(1):116 (2017).
Miller et al. Design, Construction, and In Vitro Analyses of Multivalent Antibodies. The Journal of Immunology 170:4854-4861 (2003).
Office Action dated Feb. 9, 2018 for U.S. Appl. No. 14/933,853.
Office Action dated Sep. 4, 2018 for U.S. Appl. No. 14/933,853.
Pardoll. The blockade of immune checkpoints in cancer immunotherapy. Nat Rev Cancer. 12(4):252-264 (2012).
Pardoll: The blockade of immune checkpoints in cancer immunotherapy. Nature Reviews. Cancer, GB. 12(4):252-264 doi:10.1038/nrc3239 (2012).
PCT/US2017/041256 International Search Report and Written Opinion dated Jan. 4, 2018.
PCT/US2019/012429 International Search Report and Written Opinion dated Apr. 18, 2019.
PCT/US2020/027725 International Preliminary Report on Patentability Oct. 21, 2021.
PCT/US2020/027725 International Search Report and Written Opinion dated Sep. 14, 2020.
PCT/US2021/019685 International Search Report and Written Opinion dated Jun. 14, 2021.
PCT/US2022/041395 International Search Report and Written Opinion dated Nov. 25, 2022.
PCT/US2022/041400 International Search Report and Written Opinion dated Nov. 25, 2022.
Peng, et al. PD-1 blockade enhances T-cell migration to tumors by elevating IFN-γ inducible chemokines. Cancer res, 2012, 72(20): 5209-5218.
Portolano et al.: Lack of Promiscuity In Autoantigen-specific H and L Chain Combinations as Revealed By Human H And L Chain "roulette". Journal of Immunology 150(3): 880-887 (1993).
Prado-Garcia, et al. Tumor-Induced CD8+ T-Cell Dysfunction in Lung Cancer Patients. Hindawi Publishing Corporation, Clinical and Developmental Immunology, vol. 2012, Article ID 741741, 11 pages.

(56) References Cited

OTHER PUBLICATIONS

Raje et al.: Phase 1 Study of Tabalumab, a Human Anti-B-Cell Activating Factor Antibody, and Bortezomib in Patients with Relapsed/Refractory Multiple Myeloma. Clinical Cancer Research. 22(23):5688-5695 (2016) doi:10.1158/1078-0432.CCR-16-0201.
Raje, et al. Phase 1 Study of Tabalumab, a Human Anti-B-Cell Activating Factor Antibody, and Bortezomib in Patients with Relapsed/Refractory Multiple Myeloma. Clinical Cancer Research, vol. 22, No. 23, Jun. 10, 2016 (Jun. 10, 2016), pp. 5688-5695.
Raje et al.: Phase 2 study of tabalumab, a human anti-B-cell activating factor antibody, with bortezomib and dexamethasone in patients with previously treated multiple myeloma. British Journal of Haematology. 176:783-795 (2017).
Ribas, et al. The Future of Cancer Therapy: Selecting Patients Likely to Respond to PD1/L1 Blockade. Clinical Cancer Research, American Association for Cancer Research, 2014; 4982-4984.
Ridgway et al.: 'Knobs-into-holes' engineering of antibody CH3 domains for heavy chain heterodimerization.Protein Engineering. 9(7):617-621 (1996).
Rihacek, et al. B-Cell Activating Factor as a Cancer Biomarker and Its Implications in Cancer-Related Cachexia. Biomed Res Int. 2015;2015:792187. doi: 10.1155/2015/792187. Epub Aug. 3, 2015.
Rihacek et al.: B-Cell Activating Factor as a Cancer Biomarker and Its Implications in Cancer-Related Cachexia. Biomed Research International. 9 pages (2015) doi:10.1155/2015/792187.
Rudikoff et al.: Single Amino Acid Substitution Altering Antigen-binding Specificity. PNAS USA 79(6):1979-1983 (1982).
Santos et al.: Development of More Efficacious Antibodies for Medical Therapy and Diagnosis. 60:169-194 (1998).
Smulski et al.: BAFF and BAFF-Receptor in B Cell Selection and Survival. Frontiers in Immunology. 9 (2018).
Spranger, et al. Mechanism of tumor rejection with doublets of CTLA-4, PD-1/PD-L1, or IDO blockade involves restored IL-2 production and proliferation of CD8+ T cells directly within the tumor microenvironment. J Immunother Cancer. 2014; 2:3. Published online Feb. 18, 2014. doi: 10.1186/2051-1426-2-3.
Suurs et al., A review of bispecific antibodies and antibody constructs in oncology and clinical challenges. Pharmacol Ther. 201:103-119 (2019).
Taube, et al. Association of PD-1, PD-1 ligands, and other features of the tumor immune microenvironment with response to anti-PD-1 therapy. Clinical Cancer Research. Oct. 1, 2014; 20(19): 5064-5074. doi:10.1158/1078-0432. CCR-13-3271.
Thanendrarajan et al.: Nivolumab for Treatment of Advanced, Refractory, High-Risk Multiple Myeloma. Blood. American Society of Hematology. 130:1858 (2017).
Tian et al.: A novel cancer vaccine with the ability to simultaneously produce anti-PD-1 antibody and GM-CSF in cancer cells and enhance Th1-biased antitumor immunity. Signal Transduction and Targeted Therapy. 1:16025 (2016).
Timmers et al., Chimeric antigen receptor-modified T cell therapy in multiple myeloma: beyond B cell maturation antigen. Front Immunol. 10:1613. doi: 10.3389/fimmu.2019.01613 (2019).
Totonez, M. AACR 2015: Report from Day 5. Cancer Research Institute Blog, Apr. 22, 2015.
Tumeh, Paul C, et al., PD-1 Blockade Induces Responses By Inhibiting Adaptive Immune Resistance. Nature 515(7528):568-571 (2014).
U.S. Appl. No. 16/242,333 Office Action dated Aug. 30, 2021.
U.S. Appl. No. 16/242,333 Restriction Requirement dated Apr. 13, 2021.
U.S. Appl. No. 17/229,751 Final Office Action dated Nov. 12, 2021.
U.S. Appl. No. 17/229,751 Office Action dated Aug. 6, 2021.
U.S. Appl. No. 17/229,751 Restriction Requirement dated Jun. 11, 2021.
U.S. Appl. No. 14/933,853 Office Action dated Feb. 9, 2018.
USPTO. TC1600. Kolker: Antibodies and the written description requirement of 35 U.S.C. 112(a). pp. 1-36 (2020).
Vajdos, Felix F, et al., Comprehensive Functional Maps of the Antigen-Binding Site of an Anti-ErbB2 Antibody Obtained with Shotgun Scanning Mutagenesis. Journal of Molecular Biology 320(2):415-428 (2002).
Ward et al., Binding Activities of a Repertoire of Single Immunoglobulin Variable Domains Secreted from *Escherichia coli*. Nature 341(6242):544-546 (1989).
Whitelegg et al.: WAM: An Improved Algorithm for Modelling Antibodies on the WEB. Protein Engineering 13(12):819-824 (2000).
Wu et al., Humanization Of A Murine Monoclonal Antibody By Simultaneous Optimization Of Framework And CDR residues. J Mol Biol 294(1):151-162 (Nov. 19, 1999).
Yano, et al. Spatial-temporal FUCCI imaging of each cell in a tumor demonstrates locational dependence of cell cycle dynamics and chemoresponsiveness. Cell Cycle 13:13, 2110-2119; Jul. 1, 2014.
Zagouri, et al. Emerging antibodies for the treatment of multiple myeloma. Expert Opin Emerg Drugs. Jun. 2016;21(2):225-37. doi: 10.1080/14728214.2016.1186644.
Al-Lazikani, Bissan et al. Standard Conformations for the Canonical Structures of Immunoglobulins. Journal of Molecular Biology 273(4):927-948 (1997).
Altschul, Stephen F. et al. Basic Local Alignment Search Tool. Journal of Molecular Biology 215(3):403-410 (1990).
Aminov, S. et al. GenBank Accession No. NM_001178098. Version No. NM_001178098.2. *Homo sapiens* CD19 molecule (CD19), transcript variant 1, mRNA: pp. 1-5. Record created Jun. 2, 2019. Retrieved Aug. 8, 2024. Retrieved from: https://www.ncbi.nlm.nih.gov/nuccore/NM_001178098.2.
Aminov, S. et al. GenBank Accession No. NP_001171569. Version No. NP_001171569.1. B-lymphocyte antigen CD19 isoform 1 precursor [*Homo sapiens*]: pp. 1-5. Record created May 13, 2010. Retrieved Aug. 8, 2024. Retrieved from: https://www.ncbi.nlm.nih.gov/protein/NP_001171569.1.
Brinkmann, Ulrich et al. The Making of Bispecific Antibodies. MAbs 9(2):182-212 (2017).
Chowdhury. Engineering Hot Spots for Affinity Enhancement of Antibodies. Methods Mol. Biol 207:179-196 (2008).
Cunningham, Brian C, and James A. Wells. High-resolution Epitope Mapping of hGH-receptor Interactions by Alanine-scanning Mutagenesis. Science 244(4908):1081-1085 (1989).
Duncan, Alexander R, and Greg Winter. The Binding Site for C1q on IgG. Nature 332(6166):738-740 (1988).
GenBank Accession No. NG_007275. Version No. NG_007275.1. *Homo sapiens* CD19 molecule (CD19), RefSeqGene (LRG_35) on chromosome 16: pp. 1-7. Record created Dec. 29, 2007. Retrieved Aug. 8, 2024. Retrieved from: https://www.ncbi.nlm.nih.gov/nuccore/NG_007275.1.
Gene ID: 930. CD19 molecule. pp. 1-9. Retrieved Aug. 8, 2024. Retrieved from: https://www.ncbi.nlm.nih.gov/gene/?term=930.
Gene ID: 952. CD38 molecule. pp. 1-10. Retrieved Aug. 8, 2024. Retrieved from: https://www.ncbi.nlm.nih.gov/gene/952.
Hillier, L W. et al. GenBank Accession No. NC_000004. Version No. NC_000004.12. *Homo sapiens* chromosome 4, GRCh38.p14 Primary Assembly: pp. 1-2. Record created Feb. 3, 2014. Retrieved Aug. 8, 2024. Retrieved from: https://www.ncbi.nlm.nih.gov/nuccore/NC_000004.
Hoogenboom, Hennie R. Overview Of Antibody Phage-display Technology And Its Applications. Methods In Molecular Biology 178:1-37 (2002).
Kabat, Elvin A. et al. Sequences of Proteins of Immunological Interest, Fifth Edition. Public Health Service, National Institutes of Health 1:647-669 (1991).
Kanda, Yutaka et al. Comparison of Cell Lines for Stable Production of Fucose-negative Antibodies With Enhanced ADCC. Biotechnology and Bioengineering 94(4):680-688 (2006).
Karlin S, and S.F. Altschul. Methods for assessing the statistical significance of molecular sequence features by using general scoring schemes. Proceedings of the National Academy of Sciences of the USA 87:2264-2268 (1990).
Labrijn, Aran F. et al. Bispecific antibodies: a mechanistic review of the pipeline. Nat Review Drug Discovery. 18:585-608 (2019).

(56) References Cited

OTHER PUBLICATIONS

Lefranc, Marie-Paule et al. IMGT Unique Numbering for Immunoglobulin and T Cell Receptor Variable Domains And Ig Superfamily V-like Domains. Developmental & Comparative Immunology 27(1):55-77 (2003).

Maccallum, Robert M. et al. Antibody-Antigen Interactions: Contact Analysis And Binding Site Topography. Journal of Molecular Biology 262(5):732-745 (1996).

Nguyen, C T. et al. GenBank Accession No. NM_001775. Version No. NM_001775.4. *Homo sapiens* CD38 molecule (CD38), transcript variant 1, mRNA: pp. 1-5. Record created Nov. 22, 2018. Retrieved Aug. 8, 2024. Retrieved from: https://www.ncbi.nlm.nih.gov/nuccore/NM_001775.4.

Okazaki, Akira et al. Fucose Depletion From Human IgG1 Oligosaccharide Enhances Binding Enthalpy and Association Rate Between IgG1 and FcgammaRIIIa. Journal of Molecular Biology 336(5):1239-1249 (2004).

PCT/US2022/041400 International Preliminary Report on Patentability dated Mar. 7, 2024.

PCT/US2024/020937 International Search Report and Written Opinion dated May 30, 2024.

Ripka, James et al. Two Chinese Hamster Ovary Glycosylation Mutants Affected in the Conversion of GDP-mannose to GDP-fucose. Archives of Biochemistry and Biophysics 249(2):533-545 (1986).

UniProtKB Accession No. P11836. B-lymphocyte antigen CD20. Record created Oct. 1, 1989. Retrieved Aug. 8, 2024 at URL: https://www.uniprot.org/uniprotkb/P11836/entry pp. 1-12.

U.S. Appl. No. 17/685,201 Office Action dated Jun. 7, 2024.

U.S. Appl. No. 17/685,206 Office Action dated Jun. 7, 2024.

U.S. Appl. No. 17/685,216 Office Action dated Jun. 14, 2024.

Whitelegg, Nicholas R, and Anthony R Rees. WAM: an improved algorithm for modelling antibodies on the WEB. Protein engineering 13(12):819-824 (2000).

Wright, Ann, and Sherie L. Morrison et al. Effect of Glycosylation on Antibody Function: Implications for Genetic Engineering. Trends in Biotechnology 15(1):26-32 (1997).

Xu, Jianlin et al. Antibody Charge Variant Modulation by in Vitro Enzymatic Treatment in Different Chinese Hamster Ovary Cell Cultures. Biotechnology progress 38(5): e3268, 1-11 (2022).

Xu, Jianlin et al. Productivity Improvement and Charge Variant Modulation for Intensified Cell Culture Processes by Adding a Carboxypeptidase B (Cpb) Treatment Step. Biotechnology and bioengineering 118(9):3334-3347 (2021).

Xu, Menglong. et al. Development of a novel, fully human, anti-PCSK9 antibody with potent hypolipidemic activity by utilizing phage display-based strategy. EBioMedicine 65:103250, 1-15 (2021).

Yamane-Ohnuki, Naoko et al. Establishment of FUT8 Knockout Chinese Hamster Ovary Cells: an Ideal Host Cell Line for Producing Completely Defucosylated Antibodies With Enhanced Antibody-dependent Cellular Cytotoxicity. Biotechnology and Bioengineering 87(5):614-622 (2004).

\* cited by examiner

CD19/CD38 MULTISPECIFIC ANTIBODIES

CROSS REFERENCE TO RELATED APPLICATIONS

This application claims the benefit of U.S. Provisional Application No. 63/491,441 filed on Mar. 21, 2023, and U.S. Provisional Application No. 63/590,886 filed on Oct. 17, 2023, each of which are incorporated herein by reference.

SEQUENCE LISTING

The instant application contains a Sequence Listing which has been submitted electronically in XML format and is hereby incorporated by reference in its entirety. Said XML copy, created on Aug. 15, 2024, is named 51527-716201SEQ2.xml and is 22,474 bytes in size.

BACKGROUND

Immunosuppressive B-cell populations (i.e., regulatory B cells or Bregs) are those B-Cell populations that suppress an individual's anti-tumor immune response. Therapeutics that effectively and specifically target immunosuppressive B cells can therefore be used to prevent immunosuppression and/or remove immunosuppression thereby providing effective treatments for different types of cancer.

SUMMARY

Apart from binding to the intended target molecule, antibody drugs must also satisfy specific criteria related to manufacturability, storage stability, and the absence of off-target binding. This collection of characteristics is commonly referred to as "developability." Unfortunately, there is no single parameter (e.g., assayable property) that can definitively predict developability and developability challenges based on the universe of antibodies that made their way into the clinic.

Exemplified and provided herein are multispecific antibodies having modifications that enable greater developability and manufacturability. Provided herein in one aspect is a multispecific antibody comprising: (a) a CD38 binding moiety comprising: (i) a first polypeptide comprising an immunoglobulin heavy chain variable region comprising the amino acid sequence set forth in SEQ ID NO: 1, and a heavy chain constant region wherein the heavy chain constant region lacks a C-terminal lysine residue; and (ii) a second polypeptide comprising a light chain variable region comprising the amino acid sequence set forth in SEQ ID NO: 3; and (b) a CD19 binding moiety comprising: (i) a third polypeptide comprising an immunoglobulin heavy chain variable region comprising the amino acid sequence set forth in SEQ ID NO: 2, and a heavy chain constant region wherein the heavy chain constant region lacks a C-terminal lysine residue; and (ii) a fourth polypeptide comprising a light chain variable region comprising the amino acid sequence set forth in SEQ ID NO: 3. In certain embodiments, the heavy chain constant region of the first polypeptide, the third polypeptide, or both the first polypeptide and the third polypeptide comprise a human IgG1 or a human IgG4 constant region. In certain embodiments, the polypeptide comprising a light chain variable region further comprises a light chain constant region. In certain embodiments, the second polypeptide, the fourth polypeptide or both the second polypeptide and the fourth polypeptide comprises the amino acid sequence set forth in SEQ ID NO: 6. In certain embodiments, the CD38 binding moiety comprises one or more amino acid substitutions that inhibit homodimerization of the CD38 binding moiety. In certain embodiments, the CD38 binding moiety comprises a T366W substitution according to EU numbering or T366S/L368A/Y407V substitution according to EU numbering. In certain embodiments, the CD19 binding moiety comprises one or more amino acid substitutions that inhibit homodimerization of the CD19 binding moiety. In certain embodiments, the CD19 binding moiety comprises a T366W substitution according to EU numbering or T366S/L368A/Y407V substitution according to EU numbering. In certain embodiments, the first polypeptide consists of the amino acid sequence set forth in SEQ ID NO: 4. In certain embodiments, the third polypeptide consists of the amino acid sequence set forth in SEQ ID NO: 5. In certain embodiments, a pharmaceutical composition comprises the multispecific antibody a pharmaceutically acceptable excipient, diluent, or carrier. In certain embodiments, a nucleic acid encodes the multispecific antibody. Also described herein is a method of treating a cancer in an individual in need thereof comprising administering to the individual the multispecific antibody. In certain embodiments, the cancer or tumor is a solid-tissue cancer. In certain embodiments, the solid-tissue cancer comprises breast cancer, prostate cancer, pancreatic cancer, lung cancer, kidney cancer, stomach cancer, esophageal cancer, skin cancer, colorectal cancer, or head and neck cancer. In certain embodiments, the breast cancer is triple negative breast cancer, the lung cancer is non-small cell lung cancer, the head and neck cancer is head and neck squamous cell cancer, the kidney cancer is renal cell carcinoma, the brain cancer is glioblastoma multiforme, or the skin cancer is melanoma. In certain embodiments, the cancer or tumor is a blood cancer. In certain embodiments, the blood cancer is diffuse large B cell lymphoma. In certain embodiments, the blood cancer is myeloma. In certain embodiments, the blood cancer is Burkitt's lymphoma. In certain embodiments, the blood cancer is aggressive B cell lymphoma. In certain embodiments, the aggressive B cell lymphoma comprises double hit lymphoma, double expressor lymphoma, or triple hit lymphoma. In certain embodiments, the blood cancer is relapsed or refractory. In certain embodiments, the cancer or tumor associated with CD19 positive, CD38 high, immunosuppressive B cells is a cancer or tumor that comprises CD19 positive, CD38 high, B cell infiltrates. In certain embodiments, the CD19 positive, CD38 high immunosuppressive B cells express a B cell activation marker. In certain embodiments, the B cell activation marker comprises CD30. In certain embodiments, the cancer or tumor associated with CD19 positive, CD38 high B cells expresses PD-L1. In certain embodiments, the cancer or tumor associated with CD19 positive, CD38 high B cells is associated with CD20 low or CD20 negative B cells. In certain embodiments, the CD38 high B cells express at least about 30,000 CD38 proteins on the cell surface. In certain embodiments, the CD38 high B cells express at least about 35,000 CD38 proteins on the cell surface. In certain embodiments, the CD38 high B cells express at least about 40,000 CD38 proteins on the cell surface.

In one aspect Provided herein is a common light chain bispecific antibody comprising: an anti-CD38 heavy chain variable region and an anti-CD38 heavy chain constant region, wherein the anti-CD38 heavy chain variable region comprises: (a) a heavy chain complementarity determining region 1 (HCDR1) comprising an amino acid sequence set forth in SEQ ID NO: 7, (b) a heavy chain complementarity determining region 2 (HCDR2) comprising an amino acid sequence set forth in SEQ ID NO: 8, (c) a heavy chain complementarity determining region 3 (HCDR3) comprising an amino acid sequence set forth in SEQ ID NO: 9, and a negatively-charged amino acid at heavy chain variable region position 1 per Kabat numbering, an anti-CD19 heavy chain variable region and an anti-CD19 heavy chain constant region, wherein the anti-human-CD19 heavy chain variable region comprises: (a) a heavy chain complementarity determining region 1 (HCDR1) comprising an amino acid sequence set forth in SEQ ID NO: 10, (b) a heavy chain complementarity determining region 2 (HCDR2) comprising an amino acid sequence set forth in SEQ ID NO: 11, (c) a heavy chain complementarity determining region 3 (HCDR3) comprising an amino acid sequence set forth in SEQ ID NO: 12, and a negatively-charged amino acid at heavy chain variable region position 1 per Kabat numbering, a common light chain variable region comprising: (a) a light chain complementarity determining region 1 (LCDR1) comprising an amino acid sequence set forth in SEQ ID NO: 13, (b) a light chain complementarity determining region 2 (LCDR2) comprising an amino acid sequence set forth in SEQ ID NO: 14 (AAS), and (c) a light chain complementarity determining region 3 (LCDR3) comprising an amino acid sequence set forth in SEQ ID NO: 15, wherein: the anti-CD38 heavy chain constant region and the anti-CD19 heavy chain constant region each lack a C-terminal lysine residue (e.g., K447 per EU numbering); and the common light chain bispecific antibody comprises an experimental isoelectric point (pI) of less than 9. In certain embodiments, the common light chain bispecific antibody further comprises a hydrophobic interaction chromatography (HIC) retention time of less than about 10 minutes. In certain embodiments, the terminal lysine residue is K447 per EU numbering. In certain embodiments, the anti-CD19 heavy chain variable region comprises a serine at position 84 and/or a leucine at position 108 according to Kabat numbering. In certain embodiments, the common light chain variable region comprises a histidine at position 32 according to Kabat numbering. In certain embodiments, the negatively-charged amino acid is glutamic acid. In certain embodiments, the pI is between 8 and 9. In certain embodiments, a pharmaceutical composition comprises the common light chain bispecific antibody a pharmaceutically acceptable excipient, diluent, or carrier. In certain embodiments, a nucleic acid encodes the bispecific antibody. Also Provided herein is a method of treating a cancer in an individual in need thereof comprising administering to the individual the common light chain bispecific antibody. In certain embodiments, the cancer or tumor is a solid-tissue cancer. In certain embodiments, the solid-tissue cancer comprises breast cancer, prostate cancer, pancreatic cancer, lung cancer, kidney cancer, stomach cancer, esophageal cancer, skin cancer, colorectal cancer, or head and neck cancer. In certain embodiments, the breast cancer is triple negative breast cancer, the lung cancer is non-small cell lung cancer, the head and neck cancer is head and neck squamous cell cancer, the kidney cancer is renal cell carcinoma, the brain cancer is glioblastoma multiforme, or the skin cancer is melanoma. In certain embodiments, the cancer or tumor is a blood cancer. In certain embodiments, the blood cancer is diffuse large B cell lymphoma. In certain embodiments, the blood cancer is myeloma. In certain embodiments, the blood cancer is Burkitt's lymphoma. In certain embodiments, the blood cancer is aggressive B cell lymphoma. In certain embodiments, the aggressive B cell lymphoma comprises double hit lymphoma, double expressor lymphoma, or triple hit lymphoma. In certain embodiments, the blood cancer is relapsed or refractory. In certain embodiments, the cancer or tumor associated with CD19 positive, CD38 high, immunosuppressive B cells is a cancer or tumor that comprises CD19 positive, CD38 high, B cell infiltrates. In certain embodiments, the CD19 positive, CD38 high immunosuppressive B cells express a B cell activation marker. In certain embodiments, the B cell activation marker comprises CD30. In certain embodiments, the cancer or tumor associated with CD19 positive, CD38 high B cells expresses PD-L1. In certain embodiments, the cancer or tumor associated with CD19 positive, CD38 high B cells is associated with CD20 low or CD20 negative B cells. In certain embodiments, the CD38 high B cells express at least about 30,000 CD38 proteins on the cell surface. In certain embodiments, the CD38 high B cells express at least about 35,000 CD38 proteins on the cell surface. In certain embodiments, the CD38 high B cells express at least about 40,000 CD38 proteins on the cell surface.

In another aspect Provided herein is a method of reducing an experimental isoelectric point of an antibody, the method comprising: (a) mutating a glutamine to a negatively charge amino acid at position 1 of a heavy chain variable region per Kabat numbering; and (b) removing a lysine at the C-terminal position of a heavy chain constant region. In certain embodiments, the negatively charged amino acid is glutamic acid. In certain embodiments, the antibody is a common light chain bispecific antibody comprising: an anti-CD38 heavy chain variable region, wherein the anti-CD38 heavy chain variable region comprises: (a) a heavy chain complementarity determining region 1 (HCDR1) comprising an amino acid sequence set forth in SEQ ID NO: 7, (b) a heavy chain complementarity determining region 2 (HCDR2) comprising an amino acid sequence set forth in SEQ ID NO: 8, and (c) a heavy chain complementarity determining region 3 (HCDR3) comprising an amino acid sequence set forth in SEQ ID NO: 9, an anti-CD19 heavy chain variable region, wherein the anti-human-CD19 heavy chain variable region comprises: (a) a heavy chain complementarity determining region 1 (HCDR1) comprising an amino acid sequence set forth in SEQ ID NO: 10, (b) a heavy chain complementarity determining region 2 (HCDR2) comprising an amino acid sequence set forth in SEQ ID NO: 11, and (c) a heavy chain complementarity determining region 3 (HCDR3) comprising an amino acid sequence set forth in SEQ ID NO: 12, a common light chain variable region comprising: (a) a light chain complementarity determining region 1 (LCDR1) comprising an amino acid sequence set forth in SEQ ID NO: 13, (b) a light chain complementarity determining region 2 (LCDR2) comprising an amino acid sequence set forth in SEQ ID NO: 14 (AAS), and (c) a light chain complementarity determining region 3 (LCDR3) comprising an amino acid sequence set forth in SEQ ID NO: 15.

Also Provided herein is a method of making an antibody, the method comprising harvesting a bispecific antibody of this disclosure from the supernatant of a cell line comprising a nucleic acid encoding the antibody and subjecting the supernatant to one or more purification steps.

DETAILED DESCRIPTION

Figure 1A:
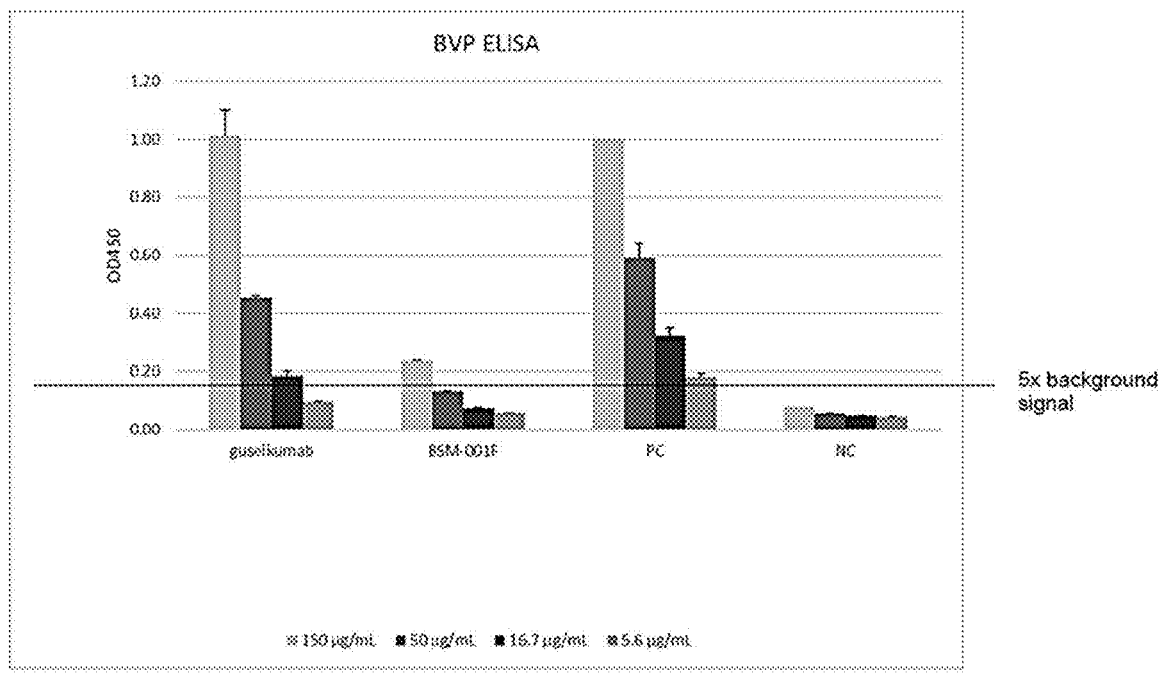
FIGS. 1A, 1B, and 1C show polyreactivity profiles for BSM-001F (BSM-001.1).

The term "immunosuppression" or "immunodepression" or "negative immune modulation", or "regulatory" in reference to particular cell populations as used herein, refers to processes or cells that are responsible for the reduction or suppression of the immune system function. Immunosuppression generally denotes a state when immune system function is reduced or absent with respect to one or functions such as cellular immunity, antibody-based immunity, or innate immune function. In certain instances, immunosuppression generally denotes a state when immune system function against a tumor or within, surrounding, or adjacent to the tumor microenvironment is reduced or absent. The whole immune response may be depressed, the immune response within a local or specific region may be reduced, or a particular population of immunologically active lymphocytes may be selectively affected. Antigen-specific immunosuppression may be the result of deletion or suppression of a particular population of antigen-specific cells, or the result of enhanced regulation of the immune response by antigen-specific suppressor cells. References to immunosuppressive B cells refer to B cells or B-cell populations that exert negative modulation on the immune response and can be identified by specific surface markers associated with such populations, such as CD38. In certain instances, immunosuppression can be identified by the presence or release of IL-10, IL-35, TGF-beta, or a combination thereof. In certain instances, immunosuppression can be identified by the presence or release by B cells of IL-10, IL-35, TGF-beta, or a combination thereof.

As used herein, the term "cancer" can refer to or describe the physiological condition in mammals that is typically characterized by unregulated cell growth. Cancer can also include, solid tumors. Cancer can refer to diseases of the blood, bones, organs, skin tissues and vascular system, including but not limited to bladder, blood, bones, brain, breast, cervix, chest, colon, endometrium, esophagus, eyes, head, kidneys, liver, lungs, lymph nodes, mouth, neck, ovaries, pancreas, prostate, rectum, kidney, skin, stomach, testes, throat and uterus. Specific cancers include, but are not limited to, gastrointestinal tumor (e.g., gastrointestinal stromal tumor (GIST)), follicular lymphoma, mantle cell lymphoma/leukemia, Diffuse B-cell lymphoma, mediastinal (thymus) large B-cell lymphoma, intravascular large B-cell lymphoma, primary exudative lymphoma, and Burkitt's lymphoma (Burkitt lymphoma), mature T cells and natural killer cell (NK) tumors (pre-lymphocytic leukemia, T-cell large lymphocytic leukemia, invasive NK cell leukemia, adult T-cell leukemia/lymphoma, Extranodal NK/T-cell lymphoma, enteropathic T-cell lymphoma, hepatosplenic T-cell lymphoma, blastic NK cell lymphoma, mycosis fungoides (Sezary syndrome), primary Skin degenerative large cell lymphoma, lymphomatoid papulosis, angioimmunoblastic T-cell lymphoma, unspecified peripheral T-cell lymphoma and degenerative large cell lymphoma, Hodgkin's lymphoma (nodular sclerosis, mixed cell type, lymphocyte rich type, lymphocyte depleted or unreduced type, nodular lymphocyte type), myeloma (multiple myeloma, inert myeloma, smoldering myeloma)), chronic myeloproliferative diseases, myelodysplasia/myeloproliferative diseases, myelodysplastic syndromes, lymphoproliferative disorders associated with immunodeficiency, histiocytic and dendritic cell tumors, Hypercytosis, chondrosarcoma, Ewing sarcoma, fibrosarcoma, malignant giant cell tumor, myeloma bone disease, osteosarcoma, breast cancer (hormone dependent, non-hormone dependent), gynecological cancer (child Cervical, endometrial, fallopian tube, gestational trophoblastic disease, ovary, peritoneum, uterus, vagina and vulva), basal cell carcinoma (BCC), squamous cell carcinoma (SCC), malignant melanoma, protuberous cutaneous fibrosarcoma, Merkel cell carcinoma, Kaposi's sarcoma, astrocytoma, hair cell astrocytoma, embryonic hair growth neuroepithelial neoplasia, oligodendroglioma, Ependymoma, glioblastoma multiforme, mixed glioma, oligodendrocyte astrocytoma, medulloblastoma, retinoblastoma, neuroblastoma, embryonal tissue tumor, teratoma, Malignant mesothelioma (peritoneal mesothelioma, pericardial mesothelioma, pleural mesothelioma), gastric-intestinal-pancreatic or gastrointestinal pancreatic neuroendocrine tumor (GEP-NET), carcinoid tumor, pancreatic endocrine tumor (PET)), colorectal adenocarcinoma, knot Rectal cancer, invasive neuroendocrine tumor, leiomyosarcoma, mucinous adenocarcinoma, signet ring cell adenocarcinoma, hepatocellular carcinoma, hepatobiliary liver cancer, hepatic blastoma, hemangioma, hepatic adenoma, focal nodular hyperplasia (nodular regenerative hyperplasia, hamartoma), non-small cell lung cancer (NSCLC) (squamous cell lung cancer, adenocarcinoma, large cell lung cancer), small cell lung cancer, thyroid cancer, prostate cancer (hormone refractory, non-androgen dependent Sex, androgen-dependent, hormone-insensitive), renal cell carcinoma and soft tissue sarcoma (fibrosarcoma, malignant fibrous histiocytoma, cutaneous fibrosarcoma, liposarcoma, rhabdomyosarcoma, leiomyosarcoma, angiosarcoma, synovial sarcoma, malignant Peripheral nerve sheath tumor/neurofibrosarcoma, extra-osseous osteosarcoma).

The term "CD19" or "Cluster of Differentiation 19" (also known as B4, T-cell surface antigen Leu-12, and CVID3) refers to a B-cell lineage surface biomarker or transmembrane protein that in humans is encoded by the gene CD19. CD19 can function as coreceptor for the B-cell antigen receptor complex (BCR) on B-lymphocytes, which decreases the threshold for activation of downstream signaling pathways and for triggering B cell responses to antigens. Structurally, a CD19 amino acid sequence has at least about 90%, 91%, 92%, 93%, 94%, 95%, 96%, 97%, 98%, 99% or 100% sequence identity with the amino acid sequence, e.g., of GenBank® accession no. NM_001178098.2→NP_001171569.1 or NM_001770.6→NP_001761.3 over a sequence length of at least 50,100,150, 200, 250, 300, 350, 400, 450, 500 amino acids or over the full length of the polypeptide. Structurally, a CD19 nucleic acid sequence has at least about 90%, 91%, 92%, 93%, 94%, 95%, 96%, 97%, 98%, 99% or 100% sequence identity with the nucleic acid sequence, e.g., of GenBank® accession no. NG_007275.1 or NCBI Gene ID 930, over a sequence length of at least 300, 500, 750, 1000, 1250, 1500 nucleic acids or over the full length of the polynucleotide. The sequence alignments can be performed using any alignment algorithm known in the art, e.g., BLAST, ALIGN, set to default settings.

The term "CD38" or "Cluster of Differentiation 38" (also known as ADPRC1) refers to a B-cell surface biomarker or transmembrane protein that in humans is encoded by the gene CD38. CD38 can function in B-cell signaling that leads to cellular activation and proliferation. Structurally, a CD38 amino acid sequence has at least about 90%, 91%, 92%, 93%, 94%, 95%, 96%, 97%, 98%, 99% or 100% sequence identity with the amino acid sequence, e.g., of GenBank® accession no. NM_001775.4→NP_001766.2 over a sequence length of at least 50, 100, 150, 200, 250, amino acids or over the full length of the polypeptide. There is a second isoform of CD38 with a premature stop codon that may be expressed at low levels in some cells. Structurally, an CD19 nucleic acid sequence has at least about 90%, 91%, 92%, 93%, 94%, 95%, 96%, 97%, 98%, 99% or 100% sequence identity with the nucleic acid sequence, e.g., of GenBank® accession no. NC_000004.12 or NCBI Gene ID 952, over a sequence length of at least 300, 500, 750 nucleic acids or over the full length of the polynucleotide. The sequence alignments can be performed using any alignment algorithm known in the art, e.g., BLAST, ALIGN, set to default settings.

The term "CD20" or "Cluster of Differentiation 20" (also known as B-lymphocyte surface antigen B1) refers to a B-cell lineage surface biomarker or transmembrane protein that in humans is encoded by the gene CD20. Structurally, a CD20 amino acid sequence has at least about 90%, 91%, 92%, 93%, 94%, 95%, 96%, 97%, 98%, 99% or 100% sequence identity with the amino acid sequence, e.g., of Uniprot entry P11836 over a sequence length of at least 50, 100, 150, 200, 250, amino acids or over the full length of the polypeptide.

As described herein with reference to binding molecules such as antibodies and bispecific antibodies "binding" refers the specific interaction of a target antigen with one or more amino acid residues of a variable region of complementarity determining region. Such specific biding will generally result in a dissociation constant of less than about $1 \times 10^{-6}$ M, such affinity can be determined by the skilled artisan using techniques known in the art, such as by surface plasmon resonance.

The term "antibody" herein is used in the broadest sense and includes multivalent or bispecific antibodies and monoclonal antibodies, including intact antibodies and functional (antigen-binding) antibody fragments thereof, including fragment antigen binding (Fab) fragments, F(ab')$_2$ fragments, Fab' fragments, Fv fragments, recombinant IgG (rIgG) fragments, single chain antibody fragments, including single chain variable fragments (sFv or scFv), and single domain antibodies (e.g., sdAb, sdFv, Nanobody®) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a human IgG1 constant region. The antibody can comprise a human IgG4 constant region.

Among the provided antibodies are multispecific or multivalent antibodies (for example, bispecific antibodies and polyreactive antibodies) and antibody fragments thereof. The antibodies include antibody-conjugates and molecules comprising the antibodies, such as chimeric molecules. Thus, an antibody includes, but is not limited to, full-length and native antibodies, as well as fragments and portion thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab')$_2$, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A monoclonal antibody can comprise a human IgG1 constant region or a human IgG4 constant region.

The terms "complementarity determining region," and "CDR" include the amino acid positions/residues (contiguous or non-contiguous) that confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme); MacCallum et al., *J. Mol. Biol.* 262:732-745 (1996), "Antibody-antigen interactions: Contact analysis and binding site topography," *J Mol. Biol.* 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Pluckthun A, "Yet another numbering scheme for immunoglobulin variable domains: an automatic modeling and analysis tool," *J Mol Biol,* 2001 Jun 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology*, 6th ed., W.H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

The term "constant region" can refer to a light chain or heavy chain constant region. Light chain constant regions have two main isotypes kappa and lambda (sometimes abbreviated CK or CL respectively). Heavy chain constant regions may comprise any one of 5 isotypes: IgA, IgD, IgG, IgE, or IgM. The IgG isotype is further comprised of IgG1, IgG2, IgG3, IgG4 subclasses. Heavy chain constant regions comprise a CH1, hinge, CH2, and/or a CH3 domain. Residues of light and heavy chain constant regions can be numbered according to the EU numbering scheme (Edelman, G. M. et al., Proc. Natl. Acad. USA, 63, 78-85 (1969).) or the Kabat numbering scheme (Kabat, E. A. et al., Sequences of proteins of immunological interest. 5th Edition—US Department of Health and Human Services, NIH publication no 91-3242, pp 662,680,689 (1991)). An "Fc Region" as described herein generally refers to the CH2 and the CH3 domains of the heavy chain constant region.

Among the provided antibodies are antibody fragments. An "antibody fragment" can refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')₂; diabodies; linear antibodies; single-chain antibody molecules (e.g. scFv or sFv); and multispecific antibodies formed from antibody fragments. In particular embodiments, the antibodies are single-chain antibody fragments comprising a variable heavy chain region and/or a variable light chain region, such as scFvs. Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., polypeptide linkers, and/or those that are not produced by enzyme digestion of a naturally-occurring intact antibody.

Herein a molecule, peptide, polypeptide, antibody, or antibody fragment can be referred to as "bispecific" or "dual-specific" including grammatical equivalents. A bispecific molecule possesses the ability to specifically bind to at least two structurally distinct targets. The specific binding may be the result of two distinct binding moieties that are structurally distinct at the molecular level, including but not limited to distinct non-identical amino acid sequences; or a single binding moiety that is able to specifically bind to two structurally distinct targets with high affinity (e.g., with a KD less than about $1\times10^{-6}$). A molecule, peptide, polypeptide, antibody, or antibody fragment referred to as "multispecific" refers to a molecule that possesses the ability to specifically bind to at least two or more structurally distinct targets. A "bispecific antibody" including grammatical equivalents refers to a bispecific molecule that preserves at least one fragment of an antibody able to specifically bind a target, for example, a variable region, heavy or light chain, or one or more complementarity determining regions from an antibody molecule. A "multispecific antibody" including grammatical equivalents refers to a multispecific molecule that preserves at least one fragment of an antibody able to specifically bind with a target, for example, a variable region, heavy or light chain, or complementarity determining region from an antibody molecule.

A "linker" herein is also referred to as "linker sequence" "spacer" "tethering sequence" or grammatical equivalents thereof. A "linker" as referred herein connects two distinct molecules that by themselves possess target binding, catalytic activity, or are naturally expressed and assembled as separate polypeptides. For example, two distinct binding moieties or a heavy-chain/light-chain pair. A number of strategies may be used to covalently link molecules together. These include but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length or about 1 to 30 amino acids in length. In one embodiment, linkers of 1 to 20 amino acids in length may be used. Useful linkers include glycine-serine polymers, including for example (GS)n, (GSGGS)n (SEQ ID NO: 22), (GGGGS)n (SEQ ID NO: 23), and (GGGS)n (SEQ ID NO: 24), where n is an integer of at least one, glycine-alanine polymers, alanine-serine polymers, and other flexible linkers. Exemplary, linkers for linking antibody fragments or single chain variable fragments can include AAEPKSS, AAEPKSSDKTH-TCPPCP (SEQ ID NO: 19), GGGG (SEQ ID NO: 20), or GGGGDKTHTCPPCP (SEQ ID NO: 21). Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers.

"Fragment-based" bispecific antibodies or bispecific antibodies comprising a "single chain variable fragment" or "scFv" of this disclosure can refer to a single chain antibody, or fragment thereof, that comprises two binding moieties and a linker connecting the two binding moieties. The linker may be a polypeptide linker or other linker of suitable flexibility so as not to inhibit binding of either targeting moiety. Fragment based bispecific antibody formats include tandem $V_{HH}$ antibodies, tandem scFvs, scFv-Fabs, F(ab)₂, dual-affinity retargeting antibodies (DARTs). Such fragment-based antibodies can be further manipulated to comprise additional binding moieties with specificity for a given target e.g., A2:B1, A1:B2 or A2:B2, or with fragments of an Fc region to improve pharmacokinetics or promote ADCC, ADCP, or CDC.

A "binding moiety" refers to a portion of a molecule, peptide, polypeptide, antibody, or antibody fragment that mediates specific binding to a recited target or antigen or epitope. By way of example, the binding moiety of an antibody may comprise a heavy-chain/light-chain variable region pair or one or more complementarity determining regions (CDRs).

A "target" as referred to herein refers to the portion of a molecule that participates with a binding moiety of a molecule, peptide, polypeptide, antibody, or antibody fragment. A target can comprise an amino acid sequence and/or a carbohydrate, lipid or other chemical entity. An "antigen" is a target comprising a portion that is able to be bound by an adaptive immune molecule such as an antibody or antibody fragment, B-cell receptor, or T-cell receptor.

In some embodiments, the bispecific antibodies provided herein have a dissociation constant ($K_D$) of about 10 µM, 1 µM, 100 nM, 50 nM, 40 nM, 30 nM, 20 nM, 10 nM, 5 nM, 2 nM, 1 nM, 0.5 nM, 0.1 nM, 0.05 nM, 0.01 nM, or 0.001 nM or less (e.g., $10^{-8}$ M or less, e.g., from $10^{-8}$ M to $10^{-13}$ M, e.g., from 10-9 M to $10^{-13}$ M) for the antibody target. The antibody target can be a CD19 target, a CD38 target, or a target comprising both CD19 and CD38. $K_D$ can be measured by any suitable assay. In certain embodiments, KD can be measured using surface plasmon resonance assays (e.g., using a BIACORE®-2000 or a BIACORE®-3000 or Octet®).

A "humanized" antibody is an antibody in which all or substantially all CDR amino acid residues are derived from non-human CDRs and all or substantially all FR amino acid residues are derived from human FRs. A humanized antibody optionally can include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

"ADCC" or "antibody dependent cell-mediated cytotoxicity" as used herein, refers to the cell-mediated reaction wherein nonspecific cytotoxic cells that express FcγRs recognize bound antibody on a target cell and subsequently cause lysis of the target cell. ADCC can be correlated with binding to FcγRIIIa wherein increased binding to FcγRIIIa leads to an increase in ADCC activity. "ADCP" or antibody dependent cell-mediated phagocytosis, as used herein, can refer to the cell-mediated reaction wherein nonspecific cytotoxic cells that express FcγRs recognize bound antibody on a target cell and subsequently cause phagocytosis of the target cell.

The terms "polypeptide" and "protein" are used interchangeably and refers to a polymer of amino acid residues, and are not limited to a minimum length. Polypeptides, including the provided antibodies and antibody chains and other peptides, e.g., linkers and binding peptides, can include amino acid residues including natural and/or non-natural amino acid residues. The terms also include post-expression modifications of the polypeptide, for example, glycosylation, sialylation, acetylation, phosphorylation, and the like. In some aspects, the polypeptides can contain modifications with respect to a native or natural sequence, as long as the protein maintains the desired activity. These modifications can be deliberate, as through site-directed mutagenesis, or can be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Amino acid sequence variants of the antibodies provided herein can be contemplated and conceived. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody amino acid sequence variants of an antibody can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Antibody variants having one or more amino acid substitutions can be provided. Sites of interest for mutagenesis by substitution include the CDRs and FRs. Amino acid substitutions can be introduced into an antibody of interest and the products screened for a desired activity, e.g., retained/improved antigen binding, decreased immunogenicity, or improved ADCC or CDC.

This disclosure also provides for "immunoconjugates" or "antibody conjugates" or "antibody-drug conjugates" that refer to an antibody conjugated to one or more heterologous molecule(s). For example, an immunoconjugate can comprise an antibody conjugated to one or more cytotoxic agents, such as chemotherapeutic agents or drugs, growth inhibitory agents, protein domains, toxins (e.g., protein toxins, enzymatically active toxins of bacterial, fungal, plant, or animal origin, or fragments thereof), or radioactive isotopes. In some embodiments, an immunoconjugate can comprise the composite binding molecule disclosed herein, or fragment thereof (e.g., an scFv).

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 1564-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large-scale cell culture are known in the art. See e.g., Li et al., "Cell culture processes for monoclonal antibody production." *Mabs*. 2010 September-October; 2(5): 466-477. In certain embodiments, the cell is a Eukaryotic cell. In certain embodiments, the Eukaryotic cell is a mammalian cell. In certain embodiments, the mammalian cell is a cell line useful for producing antibodies is a Chines Hamster Ovary cell (CHO) cell, an NS0 murine myeloma cell, or a PER.C6@ cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

As used herein the term "individual," "patient," or "subject" refers to individuals diagnosed with, suspected of being afflicted with, or at-risk of developing at least one disease for which the described compositions and method are useful for treating. In certain embodiments, the individual is a mammal. In certain embodiments, the mammal is a mouse, rat, rabbit, dog, cat, horse, cow, sheep, pig, goat, llama, alpaca, or yak. In certain embodiments, the individual is a human.

As used herein, the term "about" used to modify a specific number refers to that number plus or minus 10% of that number. The term "about" modifying a range refers to that range minus 10% of its lowest value and plus 10% of its greatest value.

As used herein, the terms "treatment" or "treating" are used in reference to a pharmaceutical or other intervention regimen used for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made. Skilled artisans will recognize that given a population of potential individuals for treatment not all will respond or respond equally to the treatment. Such individuals are considered treated.

The section headings used herein are for organizational purposes only and are not to be construed as limiting the subject matter described.

Also described herein are methods of making an antibody described herein. Such methods comprise incubating a cell or cell-line comprising a nucleic acid encoding the antibody in a cell culture medium under conditions sufficient to allow for expression and secretion of the antibody, and further harvesting the antibody from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, protein A, protein G, protein A/G, or protein L purification, and/or ion exchange chromatography.

"Treat," "treatment," or "treating," as used herein refers to, e.g., a deliberate intervention to a physiological disease state resulting in the reduction in severity of a disease or condition; the reduction in the duration of a condition course; the amelioration or elimination of one or more symptoms associated with a disease or condition; or the provision of beneficial effects to a subject with a disease or condition. Treatment does not require curing the underlying disease or condition.

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "pharmaceutically acceptable" with reference to a carrier" "excipient" or "diluent" includes any and all solvents, dispersion media, coatings, antibacterial and antifungal agents, isotonic and absorption delaying agents, and the like that are physiologically compatible. In some aspects, the carrier is suitable for intravenous, intramuscular, subcutaneous, parenteral, spinal or epidermal administration (e.g., by injection or infusion). Depending on the route of administration, the active compound, i.e., antibody, can be coated in a material to protect the compound from the action of acids and other natural conditions that can inactivate the compound.

The antibodies, bispecific, and multispecific antibodies described herein can include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Described herein in one aspect is a multispecific antibody comprising: (a) a CD38 binding moiety comprising: (i) a first polypeptide comprising an immunoglobulin heavy chain variable region comprising the amino acid sequence set forth in SEQ ID NO: 1, and a heavy chain constant region wherein the heavy chain constant region lacks a C-terminal lysine residue; and (ii) a second polypeptide comprising a light chain variable region comprising the amino acid sequence set forth in SEQ ID NO: 3; and (b) a CD19 binding moiety comprising: (i) a third polypeptide comprising an immunoglobulin heavy chain variable region comprising the amino acid sequence set forth in SEQ ID NO: 2, and a heavy chain constant region wherein the heavy chain constant region lacks a C-terminal lysine residue; and (ii) a fourth polypeptide comprising a light chain variable region comprising the amino acid sequence set forth in SEQ ID NO: 3. In certain embodiments, the heavy chain constant region of the first polypeptide, the third polypeptide, or both the first polypeptide and the third polypeptide comprise a human IgG1 or a human IgG4 constant region. In certain embodiments, the polypeptide comprising a light chain variable region further comprises a light chain constant region. In certain embodiments, the second polypeptide, the fourth polypeptide or both the second polypeptide and the fourth polypeptide comprises the amino acid sequence set forth in SEQ ID NO: 6. In certain embodiments, the CD38 binding moiety comprises one or more amino acid substitutions that inhibit homodimerization of the CD38 binding moiety. In certain embodiments, the CD38 binding moiety comprises a T366W substitution according to EU numbering or T366S/L368A/Y407V substitution according to EU numbering. In certain embodiments, the CD19 binding moiety comprises one or more amino acid substitutions that inhibit homodimerization of the CD19 binding moiety. In certain embodiments, the CD19 binding moiety comprises a T366W substitution according to EU numbering or T366S/L368A/Y407V substitution according to EU numbering. In certain embodiments, the first polypeptide consists of the amino acid sequence set forth in SEQ ID NO: 4. In certain embodiments, the third polypeptide consists of the amino acid sequence set forth in SEQ ID NO: 5. In certain embodiments, a pharmaceutical composition comprises the multispecific antibody a pharmaceutically acceptable excipient, diluent, or carrier. In certain embodiments, a nucleic acid encodes the multispecific antibody.

Bispecific antibodies according to this disclosure comprise intact antibody molecules or substantially fully intact antibody molecules, and may be asymmetric or symmetric.

Asymmetric bispecific antibodies generally comprise a heavy chain/light chain (HC/LC) pair from an antibody specific for target A and an HC/LC pair from an antibody specific for target B, creating a hetero-bifunctional antibody. Hetero-bifunctional antibodies such as these face the problem of unproductive formation of the molecule when it is being produced. HC/LC-A:HC/LC-B is desired, but is usually thermodynamically or statistically unfavorable from all the possible combinations possible. Multiple schemes have been introduced to circumvent this problem. In some instances, the HC/LC pair from an antibody with specificity for A and the HC/LC pair from an antibody with specificity for B further comprise mutations to the FC region to increase the probability of formation of an antibody with HC/LC-A: HC/LC-B. This can be achieved by engineering structural features such as "knobs" into the FC region for HC-A, and "holes" into HC-B, or vice versa, that promote formation of heterodimers between HC-A and HC-B. Another scheme to promote HC-A:HC-B heterodimers is to engineer amino acid residues in the FC portion of HC-A and HC-B to comprise charge pairs that favor electrostatic interactions between HC-B and HC-A. Another scheme to address the problem of chain association is to replace the variable regions of one of the HC/LC pairs with a single-chain binding molecules (e.g., $V_{HH}$ or an scFv). Such that one-half of the molecule comprises a classical HC/LC pair and the other comprises a HC constant region fused or otherwise connected to the single-chain binding molecule. Further modifications can be made to promote proper HC/LC paring and include engineering mutations to the HC and LC for either A or B to favor formation of the proper HC/LC pair; CrossMab technology, which entails swapping the corresponding constant regions of the HC/LC pair. Symmetric bispecific antibodies circumvent the chain association problem by not relying on formation of a hetero-bifunctional molecule. Such examples include: the dual-variable domain molecule, which comprises stacked variable regions of differing specificity; the IgG-scFv molecule, which comprises an scFv of a differing specificity fused to the c-terminus of heavy chain of a classical antibody molecule; the $(scFV)_4$-FC, which comprises two scFvs connected by an Fc region of an Ig (the Fcs dimerize creating a bispecific, tetravalent molecule); the DART-Fc and the two-in-one, amongst others.

The structure of multispecific antibodies or bispecific antibodies can be conceived and designed to alter functionality or binding properties of the composite binding molecules or bispecific antibodies (see e.g., "Bispecific antibodies: a mechanistic review of the pipeline." Nat Rev Drug Discovery. 2019 August; 18(8):585-608) (see e.g., "The making of bispecific antibodies" MAbs. 2017 February-March; 9(2): 112-212). For example, the bispecific antibody can be selected from one of the following formats: a common light chain bispecific IgG, a Fab-Fc:scFv-Fc bispecific IgG, a Fab-Fc-Fab:Fc bispecific IgG, a Fab-Fc-scFv: Fab-Fc-scFv bispecific IgG, a Fab-Fc-scFv:Fc bispecific IgG, a Fab-Fc-Fab:Fab-Fc bispecific IgG, an scFv-Fab-Fc: scFv-Fab-Fc bispecific IgG, a Fab-Fab-Fc:Fab-Fab-Fc bispecific IgG, a Fab-Fc-Fab:Fab-Fc-Fab bispecific IgG, and a Fab-Fc-scFv:Fab-Fc bispecific IgG.

Exemplary knob into hole mutations for use with antibodies described herein can comprise T366W (EU numbering) in one heavy chain and T366S/L368A/Y407V (EU numbering) in a second heavy chain. Exemplary mutations that facilitate coupling of a first and a second heavy chain molecule are disclosed, for example in WO2009089004, U.S. Pat. No. 8,642,745, US PG-PUB: US20140322756 and "The making of bispecific antibodies" MAbs. 2017 February-March; 9(2): 112-212.

In some embodiments, provided herein are common light chain bispecific antibodies comprising: (1) an anti-CD38 heavy chain variable region and an anti-CD38 heavy chain constant region, wherein the anti-CD38 heavy chain variable region comprises: (i) a heavy chain complementarity determining region 1 (HCDR1) comprising an amino acid sequence set forth in SEQ ID NO: 7, (ii) a heavy chain complementarity determining region 2 (HCDR2) comprising an amino acid sequence set forth in SEQ ID NO: 8, (iii) a heavy chain complementarity determining region 3 (HCDR3) comprising an amino acid sequence set forth in SEQ ID NO: 9, and (iv) a Q1E heavy chain variable region mutation per Kabat numbering, (2) an anti-CD19 heavy chain variable region and an anti-CD19 heavy chain constant region, wherein the anti-human-CD19 heavy chain variable region comprises: (i) a heavy chain complementarity determining region 1 (HCDRT) comprising an amino acid sequence set forth in SEQ ID NO: 10, (ii) a heavy chain complementarity determining region 2 (HCDR2) comprising an amino acid sequence set forth in SEQ ID NO: 11, (iii) a heavy chain complementarity determining region 3 (HCDR3) comprising an amino acid sequence set forth in SEQ ID NO: 12, and (iv) the Q1E heavy chain variable region mutation per Kabat numbering, (3) a common light chain variable region comprising: (i) a light chain complementarity determining region 1 (LCDRT) comprising an amino acid sequence set forth in SEQ ID NO: 13, (ii) a light chain complementarity determining region 2 (LCDR2) comprising an amino acid sequence set forth in SEQ ID NO: 14 (AAS), and (iii) a light chain complementarity determining region 3 (LCDR3) comprising an amino acid sequence set forth in SEQ ID NO: 15, wherein: the anti-CD38 heavy chain constant region and the anti-CD19 heavy chain constant region each lack a C-terminal lysine residue (e.g., K478 per Kabat numbering); and the common light chain bispecific antibody comprises an experimental isoelectric point (pI) of less than about 9. In certain instances, the anti-CD38 heavy chain variable region can comprise a heavy chain complementarity determining region 2 (HCDR2) comprising an amino acid sequence set forth in SEQ ID NO: 8 or 16-18.

In certain embodiments, the common light chain bispecific antibody further comprises a hydrophobic interaction chromatography (HIC) retention time of less than about 10 minutes. In certain embodiments, the anti-CD19 heavy chain variable region comprises a serine at position 84 and/or a leucine at position 108 according to Kabat numbering. In certain embodiments, the common light chain variable region comprises a histidine at position 32 according to Kabat numbering. In certain embodiments, the pI is less than 9. In certain embodiments, the pI is between 8 and 9. In certain embodiments, the pI is between 8.5 and 9.0. In certain embodiments, the pI is between 8.7 and 9.0. In certain embodiments, the pI is between 8.8 and 9.0. In certain embodiments, the pI is 8.9.

Therapeutic Methods

In certain embodiments, disclosed herein, are antibodies useful for the treatment of a cancer or tumor. Treatment refers to a method that seeks to improve or ameliorate the condition being treated. With respect to cancer, treatment includes, but is not limited to, reduction of tumor volume, reduction in growth of tumor volume, increase in progression-free survival, or overall life expectancy. In certain embodiments, treatment will effect remission of a cancer being treated. In certain embodiments, treatment encompasses use as a prophylactic or maintenance dose intended to prevent reoccurrence or progression of a previously treated cancer or tumor. It is understood by those of skill in the art that not all individuals will respond equally or at all to a treatment that is administered, nevertheless these individuals are considered to be treated.

Also described herein is a method of treating a cancer in an individual in need thereof comprising administering to the individual the multispecific antibody. In certain embodiments, the cancer or tumor is a solid-tissue cancer. In certain embodiments, the solid-tissue cancer comprises breast cancer, prostate cancer, pancreatic cancer, lung cancer, kidney cancer, stomach cancer, esophageal cancer, skin cancer, colorectal cancer, or head and neck cancer. In certain embodiments, the breast cancer is triple negative breast cancer, the lung cancer is non-small cell lung cancer, the head and neck cancer is head and neck squamous cell cancer, the kidney cancer is renal cell carcinoma, the brain cancer is glioblastoma multiforme, or the skin cancer is melanoma. In certain embodiments, the cancer or tumor is a blood cancer. In certain embodiments, the blood cancer is diffuse large B cell lymphoma. In certain embodiments, the blood cancer is myeloma. In certain embodiments, the blood cancer is Burkitt's lymphoma. In certain embodiments, the blood cancer is aggressive B cell lymphoma. In certain embodiments, the aggressive B cell lymphoma comprises double hit lymphoma (e.g., (e.g., defined by mutations and/or rearrangements within the MYC gene and either the BCL2 gene or the BCL6 gene), double expressor lymphoma (e.g., defined by the co-expression of c-MYC and BCL-2), or triple hit lymphoma (e.g., defined as having morphologic, biologic, and cytogenetic properties similar to both diffuse large B-cell lymphoma and Burkitt lymphoma, but possessing three, instead of two, gene rearrangements: c-MYC, BCL-2, and BCL-6 genes). In certain embodiments, the blood cancer is relapsed (e.g., the cancer has returned after a period of remission) or refractory (e.g., the cancer a stopped responding to a prior treatment with a different therapeutic/treatment). In certain embodiments, the cancer or tumor associated with CD19 positive, CD38 high, immunosuppressive B cells is a cancer or tumor that comprises CD19 positive, CD38 high, B cell infiltrates. In certain embodiments, the CD19 positive, CD38 high immunosuppressive B cells express a B cell activation marker. In certain embodiments, the B cell activation marker comprises CD30. In certain embodiments, the cancer or tumor associated with CD19 positive, CD38 high B cells expresses PD-L1. In certain embodiments, the cancer or tumor associated with CD19 positive, CD38 high B cells is associated with CD20 low or CD20 negative B cells. In certain embodiments, the CD38 high B cells express at least about 30,000 CD38 proteins on the cell surface. In certain embodiments, the CD38 high B cells express at least about 35,000 CD38 proteins on the cell surface. In certain embodiments, the CD38 high B cells express at least about 40,000 CD38 proteins on the cell surface. In certain embodiments, the multispecific antibody comprises: (a) a CD38 binding moiety comprising: (i) a first polypeptide comprising an immunoglobulin heavy chain variable region comprising the amino acid sequence set forth in SEQ ID NO: 1, and a heavy chain constant region wherein the heavy chain constant region lacks a C-terminal lysine residue; and (ii) a second polypeptide comprising a light chain variable region comprising the amino acid sequence set forth in SEQ ID NO: 3; and (b) a CD19 binding moiety comprising: (i) a third polypeptide comprising an immunoglobulin heavy chain variable region comprising the amino acid sequence set forth in SEQ ID NO: 2, and a heavy chain constant region wherein the heavy chain constant region lacks a C-terminal lysine residue; and (ii) a fourth polypeptide comprising a light chain variable region comprising the amino acid sequence set forth in SEQ ID NO: 3.

In certain embodiments, the cancer or tumor is a solid cancer or tumor. In certain embodiments, the cancer or tumor is a blood cancer or tumor. In certain embodiments, the cancer or tumor comprises breast, heart, lung, small intestine, colon, spleen, kidney, bladder, head, neck, ovarian, prostate, brain, pancreatic, skin, bone, bone marrow, blood, thymus, uterine, testicular, and liver tumors. In certain embodiments, tumors which can be treated with the antibodies of the invention comprise adenoma, adenocarcinoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and/or teratoma. In certain embodiments, the tumor/cancer is selected from the group of acral lentiginous melanoma, actinic keratosis, adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, chondrosarcoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, gastronoma, germ line tumors, glioblastoma, glucagonoma, hemangioblastoma, hemangioendothelioma, hemangioma, hepatic adenoma, hepatic adenomatosis, hepatocellular carcinoma, insulinite, intraepithelial neoplasia, intraepithelial squamous cell neoplasia, invasive squamous cell carcinoma, large cell carcinoma, liposarcoma, lung carcinoma, lymphoblastic leukemia, lymphocytic leukemia, leiomyosarcoma, melanoma, malignant melanoma, malignant mesothelial tumor, nerve sheath tumor, medulloblastoma, medulloepithelioma, mesothelioma, mucoepidermoid carcinoma, myeloid leukemia, neuroblastoma, neuroepithelial adenocarcinoma, nodular melanoma, osteosarcoma, ovarian carcinoma, papillary serous adenocarcinoma, pituitary tumors, plasmacytoma, pseudosarcoma, prostate carcinoma, pulmonary blastoma, renal cell carcinoma, retinoblastoma, rhabdomyosarcoma, sarcoma, serous carcinoma, squamous cell carcinoma, small cell carcinoma, soft tissue carcinoma, somatostatin secreting tumor, squamous carcinoma, squamous cell carcinoma, undifferentiated carcinoma, uveal melanoma, verrucous carcinoma, vagina/vulva carcinoma, VIPpoma, and Wilm's tumor. In certain embodiments, the tumor/cancer to be treated with one or more antibodies of the invention comprise brain cancer, head and neck cancer, colorectal carcinoma, acute myeloid leukemia, pre-B-cell acute lymphoblastic leukemia, bladder cancer, astrocytoma, preferably grade II, III or IV astrocytoma, glioblastoma, glioblastoma multiforme, small cell cancer, and non-small cell cancer, preferably non-small cell lung cancer, lung adenocarcinoma, metastatic melanoma, androgen-independent metastatic prostate cancer, androgen-dependent metastatic prostate cancer, prostate adenocarcinoma, and breast cancer, preferably breast ductal cancer, and/or breast carcinoma. In certain embodiments, the cancer treated with the antibodies of this disclosure comprises glioblastoma. In certain embodiments, the cancer treated with one or more antibodies of this disclosure comprises pancreatic cancer. In certain embodiments, the cancer treated with one or more antibodies of this disclosure comprises ovarian cancer. In certain embodiments, the cancer treated with one or more antibodies of this disclosure comprises lung cancer. In certain embodiments, the cancer treated with one or more antibodies of this disclosure comprises prostate cancer. In certain embodiments, the cancer treated with one or more antibodies of this disclosure comprises colon cancer. In certain embodiments, the cancer treated comprises glioblastoma, pancreatic cancer, ovarian cancer, colon cancer, prostate cancer, or lung cancer. In a certain embodiment, the cancer is refractory to other treatment. In a certain embodiment, the cancer treated is relapsed.

In certain embodiments, the antibodies can be administered to a subject in need thereof by any route suitable for the administration of antibody-containing pharmaceutical compositions, such as, for example, subcutaneous, intraperitoneal, intravenous, intramuscular, intratumoral, or intracerebral, etc. In certain embodiments, the antibodies are administered intravenously. In certain embodiments, the antibodies are administered subcutaneously. In certain embodiments, the antibodies are administered intratumoral. In certain embodiments, the antibodies are administered on a suitable dosage schedule, for example, weekly, twice weekly, monthly, twice monthly, once every two weeks, once every three weeks, or once a month etc. In certain embodiments, the antibodies are administered once every three weeks. The antibodies can be administered in any therapeutically effective amount. In certain embodiments, the therapeutically acceptable amount is between about 0.1 mg/kg and about 50 mg/kg. In certain embodiments, the therapeutically acceptable amount is between about 1 mg/kg and about 40 mg/kg. In certain embodiments, the therapeutically acceptable amount is between about 1 mg/kg and about 20 mg/kg. In certain embodiments, the therapeutically acceptable amount is between about 1 mg/kg and about 10 mg/kg. In certain embodiments, the therapeutically acceptable amount is between about 5 mg/kg and about 30 mg/kg. In certain embodiments, the therapeutically acceptable amount is between about 5 mg/kg and about 20 mg/kg. Therapeutically effective amounts include amounts sufficient to ameliorate one or more symptoms associated with the disease or affliction to be treated.

Methods of Making pI Reduced Antibodies

In some embodiments, provided herein are methods of reducing an experimental isoelectric point of an antibody, the method comprising: (a) mutating a glutamine to a negatively charge amino acid at position 1 of a heavy chain variable region per Kabat numbering; and (b) removing a lysine at the C-terminal position of a heavy chain constant region. In some embodiments, the negatively charged amino acid is the glutamic acid. In some embodiments, the negatively charged amino acid is the aspartic acid. In some embodiments, the lysine at the C-terminal position of a heavy chain constant region is K447 per EU numbering.

In some embodiments, the antibody is a common light chain bispecific antibody comprising: (1) an anti-CD38 heavy chain variable region, wherein the anti-CD38 heavy chain variable region comprises: (i) a heavy chain complementarity determining region 1 (HCDRT) comprising an amino acid sequence set forth in SEQ ID NO: 7, (ii) a heavy chain complementarity determining region 2 (HCDR2) comprising an amino acid sequence set forth in SEQ ID NO: 8, and (iii) a heavy chain complementarity determining region 3 (HCDR3) comprising an amino acid sequence set forth in SEQ ID NO: 9, (2) an anti-CD19 heavy chain variable region, wherein the anti-human-CD19 heavy chain variable region comprises: (i) a heavy chain complementarity determining region 1 (HCDR1) comprising an amino acid sequence set forth in SEQ ID NO: 10, (ii) a heavy chain complementarity determining region 2 (HCDR2) comprising an amino acid sequence set forth in SEQ ID NO: 11, and (iii) a heavy chain complementarity determining region 3 (HCDR3) comprising an amino acid sequence set forth in SEQ ID NO: 12, and (3) a common light chain variable region comprising: (i) a light chain complementarity determining region 1 (LCDRT) comprising an amino acid sequence set forth in SEQ ID NO: 13, (ii) a light chain complementarity determining region 2 (LCDR2) comprising an amino acid sequence set forth in SEQ ID NO: 14 (AAS), and (iii) a light chain complementarity determining region 3 (LCDR3) comprising an amino acid sequence set forth in SEQ ID NO: 15.

In certain embodiments, the common light chain bispecific antibody further comprises a hydrophobic interaction chromatography (HIC) retention time of less than about 10 minutes. In certain embodiments, the anti-CD19 heavy chain variable region comprises a serine at position 84 and/or a leucine at position 108 according to Kabat numbering. In certain embodiments, the common light chain variable region comprises a histidine at position 32 according to Kabat numbering. In certain embodiments, the pI is less than 9. In certain embodiments, the pI is between 8 and 9. In certain embodiments, the pI is between 8.5 and 9.0. In certain embodiments, the pI is between 8.7 and 9.0. In certain embodiments, the pI is between 8.8 and 9.0. In certain embodiments, the pI is 8.9.

Pharmaceutically Acceptable Excipients, Carriers, and Diluents

In certain embodiments the multispecific antibodies of the current disclosure are included in a pharmaceutical composition comprising one or more pharmaceutically acceptable excipients, carriers, and diluents. Pharmaceutically acceptable excipients, carriers and diluents can be included to increase shelf-life, stability, or the administrability of the antibody. Such compounds include salts, pH buffers, detergents, anti-coagulants, and preservatives. In certain embodiments, the antibodies of the current disclosure are administered suspended in a sterile solution. In certain embodiments, the solution comprises about 0.9% NaCl. In certain embodiments, the solution comprises about 5.0% dextrose. In certain embodiments, the solution further comprises one or more of buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA.

In certain embodiments, the antibodies of the current disclosure can be shipped/stored lyophilized and reconstituted before administration. In certain embodiments, lyophilized antibody formulations comprise a bulking agent such as, mannitol, sorbitol, sucrose, trehalose, dextran 40, or combinations thereof. The lyophilized formulation can be contained in a vial comprised of glass or other suitable non-reactive material. The antibodies when formulated, whether reconstituted or not, can be buffered at a certain pH, generally less than 7.0. In certain embodiments, the pH can be between 4.5 and 7.0, 4.5 and 6.5, 4.5 and 6.0, 4.5 and 5.5, 4.5 and 5.0, or 5.0 and 6.0.

Also described herein are kits comprising one or more of the antibodies described herein in a suitable container and one or more additional components selected from: instructions for use; a diluent, an excipient, a carrier, and a device for administration.

In certain embodiments, described herein is a method of preparing a cancer treatment comprising admixing one or more pharmaceutically acceptable excipients, carriers, or diluents and an antibody of the current disclosure. In certain embodiments, described herein is a method of preparing a cancer treatment for storage or shipping comprising lyophilizing one or more antibodies of the current disclosure.

ADDITIONAL EXEMPLARY EMBODIMENTS

Exemplary embodiment 1. A common light chain bispecific antibody comprising: an anti-CD38 heavy chain variable region and an anti-CD38 heavy chain constant region, wherein the anti-CD38 heavy chain variable region comprises: a heavy chain complementarity determining region 1 (HCDRT) comprising an amino acid sequence set forth in SEQ ID NO: 7, a heavy chain complementarity determining region 2 (HCDR2) comprising an amino acid sequence set forth in SEQ ID NO: 8, a heavy chain complementarity determining region 3 (HCDR3) comprising an amino acid sequence set forth in SEQ ID NO: 9, and a negatively-charged amino acid at heavy chain variable region position 1 per Kabat numbering, an anti-CD19 heavy chain variable region and an anti-CD19 heavy chain constant region, wherein the anti-human-CD19 heavy chain variable region comprises: a heavy chain complementarity determining region 1 (HCDR1) comprising an amino acid sequence set forth in SEQ ID NO: 10,
a heavy chain complementarity determining region 2 (HCDR2) comprising an amino acid sequence set forth in SEQ ID NO: 11, a heavy chain complementarity determining region 3 (HCDR3) comprising an amino acid sequence set forth in SEQ ID NO: 12, and a negatively-charged amino acid at heavy chain variable region position 1 per Kabat numbering, a common light chain variable region comprising: a light chain complementarity determining region 1 (LCDRT) comprising an amino acid sequence set forth in SEQ ID NO: 13, a light chain complementarity determining region 2 (LCDR2) comprising an amino acid sequence set forth in SEQ ID NO: 14, and a light chain complementarity determining region 3 (LCDR3) comprising an amino acid sequence set forth in SEQ ID NO: 15, wherein: the anti-CD38 heavy chain constant region and the anti-CD19 heavy chain constant region each lack a C-terminal lysine residue; and the common light chain bispecific antibody comprises an experimental isoelectric point (pI) of less than 9.0, preferably wherein the common light chain bispecific antibody also comprises a hydrophobic interaction chromatography (HIC) retention time of less than about 10 minutes (e.g., as assayed in Example 2).

Exemplary embodiment 2. The common light chain bispecific antibody of embodiment 1, wherein the common light chain bispecific antibody further comprises a hydrophobic interaction chromatography (HIC) retention time of less than about 10 minutes (e.g., as assayed in Example 2).

Exemplary embodiment 3. The common light chain bispecific antibody of any one of embodiments 1-2, wherein the terminal lysine residue is K447 per EU numbering.

Exemplary embodiment 4. The common light chain bispecific antibody of any one of embodiments 1-3, wherein the anti-CD19 heavy chain variable region comprises a serine at position 84 and/or a leucine at position 108 according to Kabat numbering.

Exemplary embodiment 5. The common light chain bispecific antibody of any one of embodiments 1-4, wherein the common light chain variable region comprises a histidine at position 32 according to Kabat numbering.

Exemplary embodiment 6. The common light chain bispecific antibody of any one of embodiments 1-5, wherein the negatively-charged amino acid is glutamic acid.

Exemplary embodiment 7. The common light chain bispecific antibody of any one of embodiments 1-6, wherein the pI is between 8.7 and 9.0.

Exemplary embodiment 8. The common light chain bispecific antibody of any one of embodiments 1-7, wherein the anti-CD19 heavy chain constant region comprises a T366W substitution according to EU numbering or T366S/L368A/Y407V substitution according to EU numbering.

Exemplary embodiment 9. The common light chain bispecific antibody of any one of embodiments 1-8, wherein the anti-CD38 heavy chain constant region comprises a T366W substitution according to EU numbering or T366S/L368A/Y407V substitution according to EU numbering.

Exemplary embodiment 10. The common light chain bispecific antibody of any one of embodiments 1-9, wherein common light chain bispecific antibody further comprises a light chain constant region.

Exemplary embodiment 11. The common light chain bispecific antibody of any one of embodiments 1-10, wherein:
(i) the anti-CD38 heavy chain variable region and the anti-CD38 heavy chain constant comprise the amino acid sequence of SEQ ID NO: 4;
(ii) the anti-CD19 heavy chain variable region and the anti-CD38 heavy chain constant comprise the amino acid sequence of SEQ ID NO: 5;
(iii) the common light chain variable region and the light chain constant region comprise the amino acid sequence of SEQ ID NO: 6.

Exemplary embodiment 12. A composition comprising one or more nucleic acid molecules encoding the common light chain bispecific antibody of any one of embodiments 1-11.

Exemplary embodiment 13. A cell comprising one or more one nucleic acid molecules encoding the common light chain bispecific antibody of any one of embodiments 1-11.

Exemplary embodiment 14. A method of treating a cancer in an individual in need thereof comprising administering to the individual the common light chain bispecific antibody of any one of embodiments 1-11.

Exemplary embodiment 15. The method of embodiment 14, wherein the cancer comprises a solid tumor.

Exemplary embodiment 16. The method of embodiment 14, wherein the cancer is a hematological cancer.

Exemplary embodiment 17. The method of embodiment 16, wherein the hematological cancer is a B cell malignancy.

Exemplary embodiment 18. A method of reducing an experimental isoelectric point of an antibody, the method comprising:
(a) mutating a glutamine to a negatively charge amino acid at position 1 of a heavy chain variable region per Kabat numbering; and (b) removing a lysine at the C-terminal position of a heavy chain constant region,
wherein the antibody is a common light chain bispecific antibody comprising: an anti-CD38 heavy chain variable region and an anti-CD38 heavy chain constant region, wherein the anti-CD38 heavy chain variable region comprises: a heavy chain complementarity determining region 1 (HCDRT) comprising an amino acid sequence set forth in SEQ ID NO: 7, a heavy chain complementarity determining region 2 (HCDR2) comprising an amino acid sequence set forth in SEQ ID NO: 8, and a heavy chain complementarity determining region 3 (HCDR3) comprising
an amino acid sequence set forth in SEQ ID NO: 9, an anti-CD19 heavy chain variable region and an anti-CD19 heavy chain constant region, wherein the antihuman-CD19 heavy chain variable region comprises: a heavy chain complementarity determining region 1 (HCDR1) comprising an amino acid sequence set forth in SEQ ID NO: 10, a heavy chain complementarity determining region 2 (HCDR2) comprising an amino acid sequence set forth in SEQ ID NO: 11, and a heavy chain complementarity determining region 3 (HCDR3) comprising an amino acid sequence set forth in SEQ ID NO: 12, a common light chain variable region comprising: a light chain complementarity determining region 1 (LCDR1) comprising an amino acid sequence set forth in SEQ ID NO: 13, a light chain complementarity determining region 2 (LCDR2) comprising an amino acid sequence set forth in SEQ ID NO: 14, and a light chain complementarity determining region 3 (LCDR3) comprising an amino acid sequence set forth in SEQ ID NO: 15.

EXAMPLES

Example 1

Polyspecificity was measured using ELISA (BVP, PSR HEK293, PSR CHO). Plates (3) were coated with Baculovirus particle (BVP), HEK293, and CHO at 4° C. overnight. Antibody concentration of 150, 50, 16.7 and 5.6 ug/mL were tested in triplicate. Plates were blocked (Blocking buffer: PBS+2% BSA). Background signal was measured against coated wells with secondary (2nd) Ab only. A cut off of 5×background signal was used. Positive control (PC) included MEDNA Bio #H1308 and negative control (NC) included MEDNA Bio #H1314.

BSM-001F (BSM-001.1) is a common light chain antibody comprising: (1) an anti-CD38 heavy chain variable region and an anti-CD38 heavy chain constant region, wherein the anti-CD38 heavy chain variable region comprises (i) a heavy chain complementarity determining region 1 (HCDR1) comprising an amino acid sequence set forth in SEQ ID NO: 7, (ii) a heavy chain complementarity determining region 2 (HCDR2) comprising an amino acid sequence set forth in SEQ ID NO: 8, (iii) a heavy chain complementarity determining region 3 (HCDR3) comprising an amino acid sequence set forth in SEQ ID NO: 9, (2) an anti-CD19 heavy chain variable region and an anti-CD19 heavy chain constant region, wherein the anti-human-CD19 heavy chain variable region comprises (i) a heavy chain complementarity determining region 1 (HCDR1) comprising an amino acid sequence set forth in SEQ ID NO: 10, (ii) a heavy chain complementarity determining region 2 (HCDR2) comprising an amino acid sequence set forth in SEQ ID NO: 11, and (iii) a heavy chain complementarity determining region 3 (HCDR3) comprising an amino acid sequence set forth in SEQ ID NO: 12, (3) a common light chain variable region comprising: (i) a light chain complementarity determining region 1 (LCDR1) comprising an amino acid sequence set forth in SEQ ID NO: 13, (ii) a light chain complementarity determining region 2 (LCDR2) comprising an amino acid sequence set forth in SEQ ID NO: 14 (AAS), and (iii) a light chain complementarity determining region 3 (LCDR3) comprising an amino acid sequence set forth in SEQ ID NO: 15. BSM-001F includes a Q1E heavy chain variable region mutation per Kabat numbering in each heavy chain, the anti-CD38 heavy chain constant region, and the anti-CD19 heavy chain constant region each lack a C-terminal lysine residue (e.g., K447 per EU numbering).

Figure 1B:
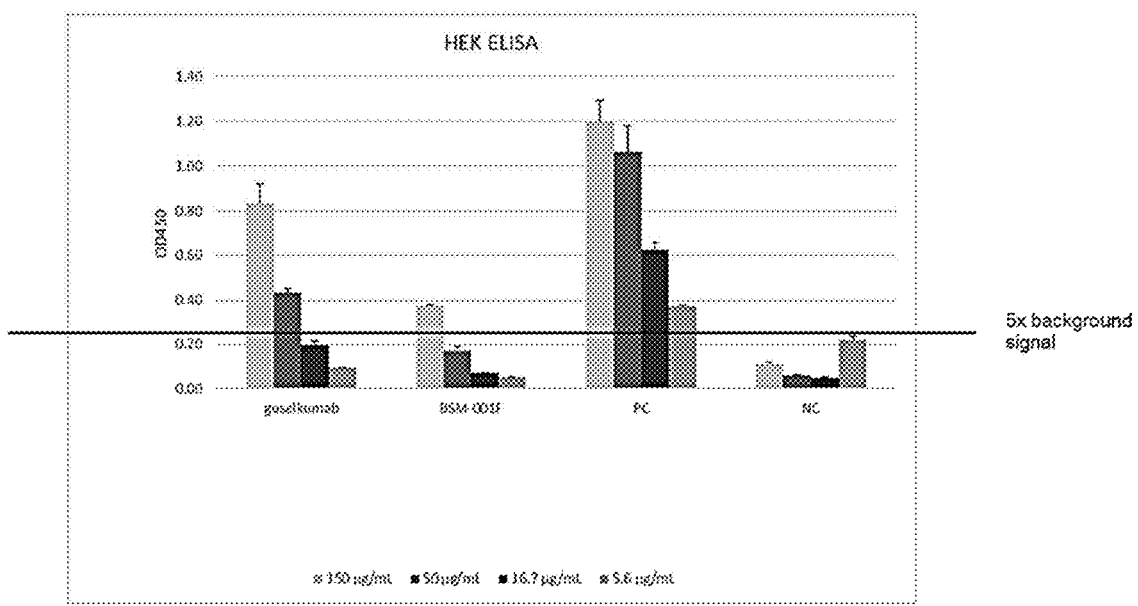
Figure 1C:
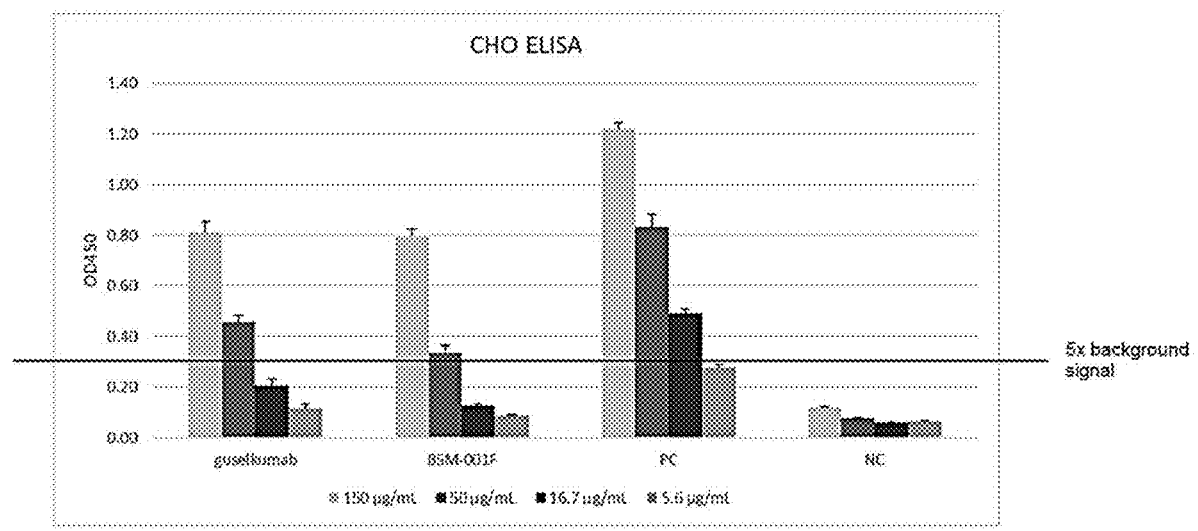

For data analysis a BVP/HEK/CHO score was determined, wherein the BVP/HEK/CHO Score=(Average OD450 value of triplicated sample)/(Average OD450 value of background signal). FIGS. 1A-C show ELISA OD450 readings for guselkumab, BSM-001F (BSM-001.1), NC, and PC. BSM-001F (BSM-001.1) exhibited substantially lower polyreactivity when compared to guselkumab and PC.

Example 2

To determine the experimental isoelectric point, the sample was diluted in a matrix of methyl cellulose, 4 M urea, 3-10 pharmalytes (4%), 5 mM Arginine, and pI markers (at pI 4.22 and pI 10.10). The mixture was submitted to an iCE3 IEF Analyzer (ProteinSimple™) and pre-focused at 1,500 V followed by focusing at 3,000 V. The isoelectric points of each peak were calculated from the bracketing pI markers. The experimental isoelectric point of BSM-001F (BSM-001.1) was measured to be 8.9. Unmodified BSM-001 (i) lacking a negatively-charged amino acid at heavy chain variable region position 1 per Kabat numbering and (ii) having heavy chain constant regions that include a terminal lysine residue (e.g., K447 per EU numbering) exhibited a pI of 9.1. The experimental isoelectric point of BSM-001F (BSM-001.1) was lowered below 9 (8.9).

Figure 2:
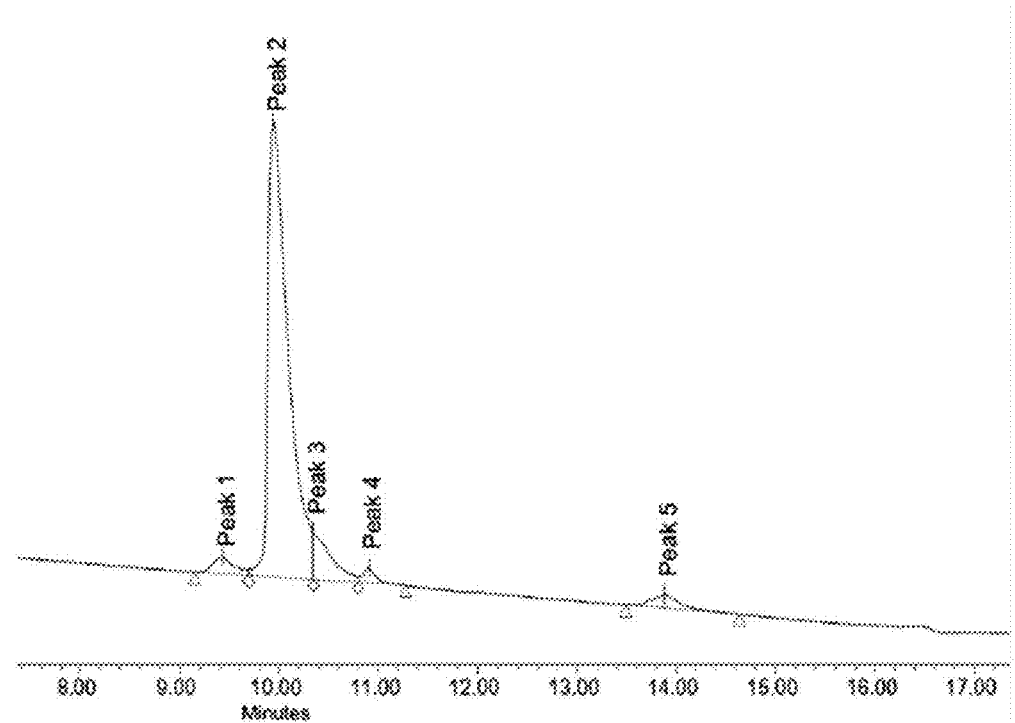
FIG. 2 shows hydrophobic interaction chromatography (HIC) profiles for BSM-001F (BSM-001.1).

Curia® Hydrophobic Interaction Chromatography (HIC) (Curia®) was also determined. For the HIC protocol, sample was titrated with 1M $(NH_4)_2SO_4$ before injection. 10 μL of sample was injected into a Sepax Proteomix® HIC butyl-NP1.7, 4.6×35 mm column with a flow of 0.8 mL/min. Mobile phase started as 60% of Buffer C (1.8 M $(NH_4)_2SO_4$, 0.1 M NaH2PO4, pH 6.5) and 40% of Buffer D (0.1M NaH2PO4, pH 6.5) and changed in linear gradient to 0% of buffer C and 100% of buffer D from 1 min to 16 min. Signal was measured at 280 nm. A HIC retention time of 9.9 was observed. FIG. 2 shows HIC profiles of BSM-001F (BSM-001.1).

Example 3

Figure 3:
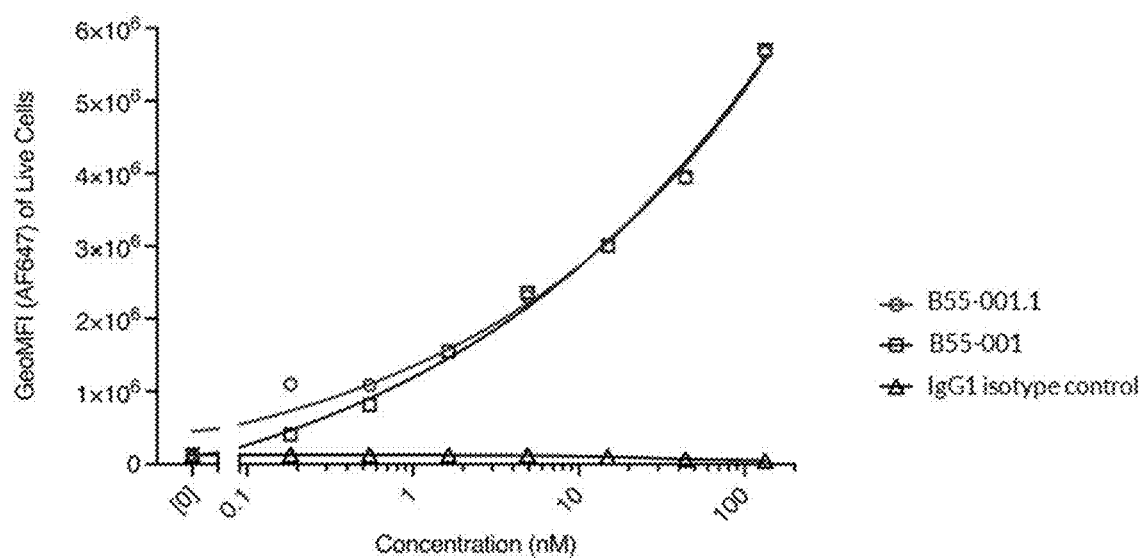
FIG. 3 shows B cell binding data for BSM-001F (BSM-001.1).

Cell binding to Daudi cells was measured. BSM-001F (BSM-001.1) showed equivalent binding to Daudi cells when compared to unmodified BSM-001 (e.g., lacking Q1E and terminal lysine modifications). FIG. 3 shows cell binding profiles.

Figure 4:
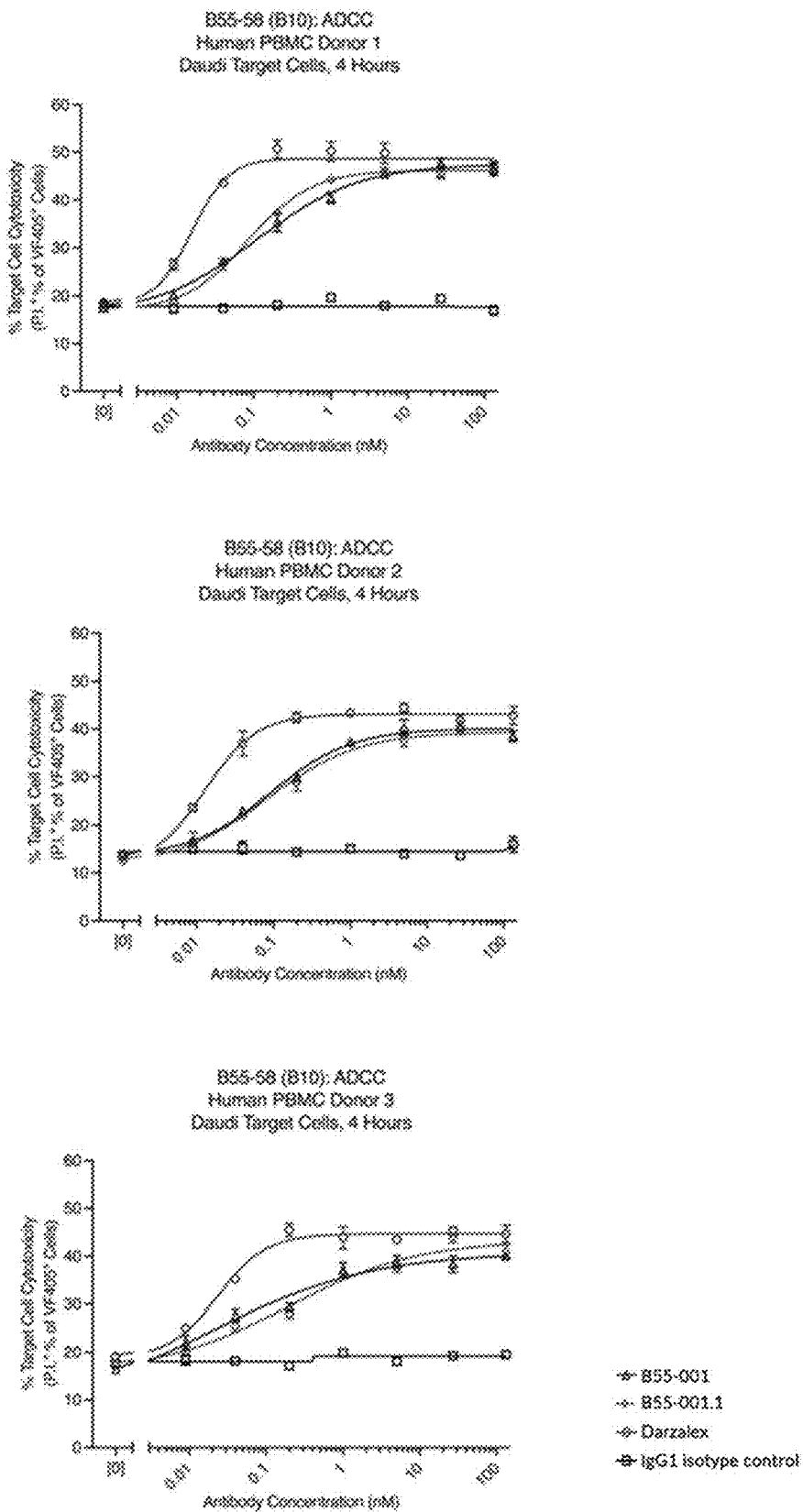
FIG. 4 shows ADCC cell killing data for BSM-001F (BSM-001.1).

ADCC killing assays were also conducted using human donor PBMC samples. For assessment of direct apoptosis, cells were treated with test articles and incubated for 48 hours at 37° C./5% $CO_2$. For assessment of cross-linking induced apoptosis, cells were incubated with test articles on ice for 30 minutes prior to the addition of rabbit anti-human Fc gamma specific F(ab')2. Cells were then incubated at 37° C./5% $CO_2$. After incubation, cells were washed and stained with Annexin V, then resuspended in Annexin V buffer containing a viability dye (propidium iodide; PI) prior to flow cytometry acquisition. Early apoptotic cells were defined as Annexin V+/PI− single cells, while late apoptotic/necrotic cells were defined as Annexin V+/PI+ single cells. The sum of Annexin V+/PI− and Annexin V+/PI− were defined as total apoptotic/necrotic cells. The percentages of Annexin V+/PI− cells or Annexin V+/PI+ were plotted to compare the various apoptosis conditions. BSM-001F (BSM-001.1) showed equivalent ADCC-mediated killing of Daudi cells when compared to unmodified BSM-001 (e.g., lacking QIE and terminal lysine modifications). FIG. 4 shows ADCC profiles.

Figure 5:
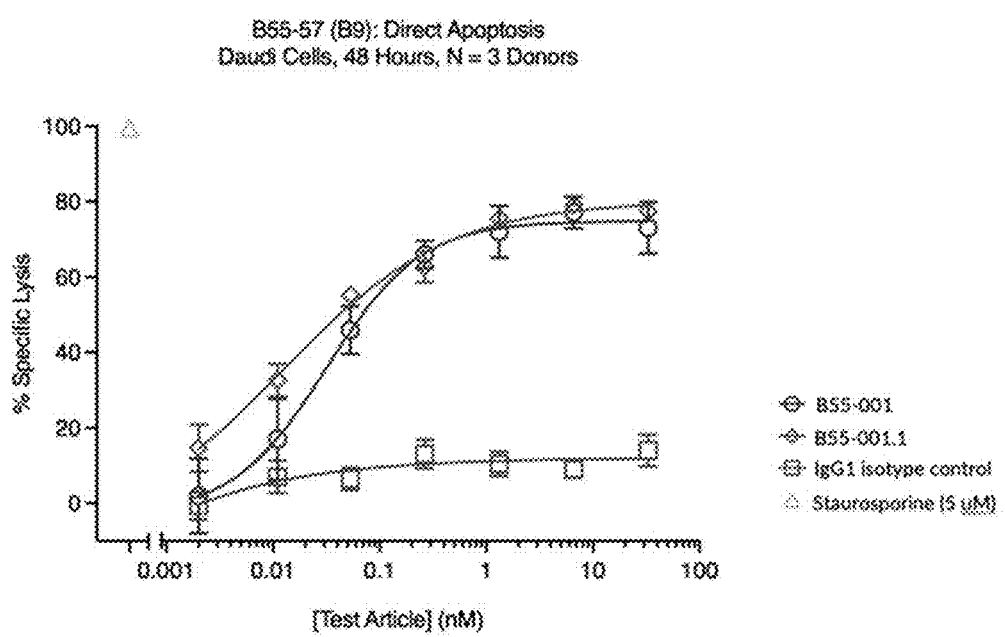
FIG. 5 shows apoptosis cell killing data for BSM-001F (BSM-001.1).

For assessment of direct apoptosis, cells were treated with test articles and incubated for 48 hours at 37° C./5% $CO_2$. For assessment of cross-linking induced apoptosis, cells were incubated with test articles on ice for 30 minutes prior to the addition of rabbit anti-human Fc gamma specific F(ab')2. Cells were then incubated for 48 hours at 37 C/5% $CO_2$. After incubation, cells were washed and stained with Annexin V, then resuspended in Annexin V buffer containing a viability dye (propidium iodide; PI) prior to flow cytometry acquisition. Early apoptotic cells were defined as Annexin V+/PI− single cells, while late apoptotic/necrotic cells were defined as Annexin V+/PI+ single cells. The sum of Annexin V+/PI− and Annexin V+/PI− were defined as total apoptotic/necrotic cells. The percentages of Annexin V+/PI− cells or Annexin V+/PI+ were plotted to compare the various apoptosis conditions. BSM-001F (BSM-001.1) showed equivalent apoptosis-mediated killing of Daudi cells when compared to unmodified BSM-001 (e.g., lacking Q1E and terminal lysine modifications). FIG. 5 shows apoptosis profiles.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

SEQUENCES
Sequence listings provided herein

| SEQ ID NO: | Sequence | Origin |
| --- | --- | --- |
| 1 | EVQLVQSGAEVKKPGSSVKVSCKASGGTFSSYAFSWVRQAPG QGLEWMGRVIPQLGIANSAQKFQGRVTITADKSTSTAYMELSS LRSEDTAVYYCARDDIAALGPFDYWGQGTLVTVSS | Anti-CD38 knob (variable region) |
| 2 | EVQLVQSGAEVKKPGSSVKVSCKASGGTFSSYTINWVRQAPGQ GLEWMGGIIPIFGIPNYAQKFQGRVTITADESTNTAYMELSSLRS EDTAVYYCARASGGSADYSYGMDVWGQGTLVTVSS | Anti-CD19 Hole (variable region) |
| 3 | DIQMTQSPSSLSASVGDRVTITCRASQGISSWLAWYQQKPEKAP KSLIYAASSLQSGVPSRFSGSGSGTDFTLTISSLQPEDFATYYCQ QYNSYPRTFGQGTKVEIK | Anti-CD38 light chain (variable region) |
| 4 | EVQLVQSGAEVKKPGSSVKVSCKASGGTFSSYAFSWVRQAPG QGLEWMGRVIPQLGIANSAQKFQGRVTITADKSTSTAYMELSS LRSEDTAVYYCARDDIAALGPFDYWGQGTLVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDK KVEPKSCDKTHTCPPCPAPELLGGPSVFLFPPKPKDTLMISRTPE VTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLWCLVKGFYPSDIAVEWESNGQ PENNYKTTPPVLDSDGSFFLYSKLTVDKSRWQQGNVFSCSVMH EALHNHYTQKSLSLSPG | Anti-CD38 bispecific arm Knob |
| 5 | EVQLVQSGAEVKKPGSSVKVSCKASGGTFSSYTINWVRQAPGQ GLEWMGGIIPIFGIPNYAQKFQGRVTITADESTNTAYMELSSLRS EDTAVYYCARASGGSADYSYGMDVWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISRT PEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSRDELTKNQVSLSCAVKGFYPSDIAVEWESNG QPENNYKTTPPVLDSDGSFFLVSKLTVDKSRWQQGNVFSCSVM HEALHNHYTQKSLSLSPG | Anti-CD19 bispecific arm Hole |
| 6 | DIQMTQSPSSLSASVGDRVTITCRASQGISSWLAWYQQKPEKAP KSLIYAASSLQSGVPSRFSGSGSGTDFTLTISSLQPEDFATYYCQ QYNSYPRTFGQGTKVEIKRTVAAPSVFIFPPSDEQLKSGTASVV CLLNNFYPREAKVQWKVDNALQSGNSQESVTEQDSKDSTYSLS STLTLSKADYEKHKVYACEVTHQGLSSPVTKSFNRGEC | Anti-CD38 light chain |
| 7 | SYAFS | Anti-CD38_VH_CDR1_ |

-continued

| SEQ ID NO: | Sequence | Origin |
|---|---|---|
| 8 | PQLGIA | Anti-CD38_VH_CDR2_ |
| 9 | DIAALGPFD | Anti-CD38_VH_CDR3_ |
| 10 | SYTIN | Anti-CD19_VH_CDR1_ |
| 11 | PIFG | Anti-CD19_VH_CDR2_ |
| 12 | SGGSADYSYGMD | Anti-CD19_VH_CDR3_ |
| 13 | SQGISSW | Anti-CD38_VL_CDR1_ |
| 14 | AAS | Anti-CD38_VL_CDR2_ |
| 15 | YNSYPR | Anti-CD38_VH_CDR3_ |
| 16 | PFLGIA | Anti-CD38_VH_CDR2 |
| 17 | PHLGIA | Anti-CD38_VH_CDR2 |
| 18 | PFLGTA | Anti-CD38_VH_CDR2 |
| 19 | AAEPKSSDKTHTCPPCP | |
| 20 | GGGG | |
| 21 | GGGGDKTHTCPPCP | |

SEQUENCE LISTING

```
Sequence total quantity: 24
SEQ ID NO: 1            moltype = AA  length = 120
FEATURE                 Location/Qualifiers
source                  1..120
                        mol_type = protein
                        organism = synthetic construct
SEQUENCE: 1
EVQLVQSGAE VKKPGSSVKV SCKASGGTFS SYAFSWVRQA PGQGLEWMGR VIPQLGIANS   60
AQKFQGRVTI TADKSTSTAY MELSSLRSED TAVYYCARDD IAALGPFDYW GQGTLVTVSS  120

SEQ ID NO: 2            moltype = AA  length = 123
FEATURE                 Location/Qualifiers
source                  1..123
                        mol_type = protein
                        organism = synthetic construct
SEQUENCE: 2
```

```
                                    -continued

EVQLVQSGAE VKKPGSSVKV SCKASGGTFS SYTINWVRQA PGQGLEWMGG IIPIFGIPNY    60
AQKFQGRVTI TADESTNTAY MELSSLRSED TAVYYCARAS GGSADYSYGM DVWGQGTLVT   120
VSS                                                                123

SEQ ID NO: 3               moltype = AA   length = 107
FEATURE                    Location/Qualifiers
source                     1..107
                           mol_type = protein
                           organism = synthetic construct
SEQUENCE: 3
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNSYPRTFGQ GTKVEIK                 107

SEQ ID NO: 4               moltype = AA   length = 449
FEATURE                    Location/Qualifiers
source                     1..449
                           mol_type = protein
                           organism = synthetic construct
SEQUENCE: 4
EVQLVQSGAE VKKPGSSVKV SCKASGGTFS SYAFSWVRQA PGQGLEWMGR VIPQLGIANS    60
AQKFQGRVTI TADKSTSTAY MELSSLRSED TAVYYCARDD IAALGPFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLWC LVKGFYPSDI AVEWESNGQP ENNYKTTPPV LDSDGSFFLY SKLTVDKSRW   420
QQGNVFSCSV MHEALHNHYT QKSLSLSPG                                    449

SEQ ID NO: 5               moltype = AA   length = 452
FEATURE                    Location/Qualifiers
source                     1..452
                           mol_type = protein
                           organism = synthetic construct
SEQUENCE: 5
EVQLVQSGAE VKKPGSSVKV SCKASGGTFS SYTINWVRQA PGQGLEWMGG IIPIFGIPNY    60
AQKFQGRVTI TADESTNTAY MELSSLRSED TAVYYCARAS GGSADYSYGM DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LSCAVKGFYP SDIAVEWESN GQPENNYKTT PPVLDSDGSF FLVSKLTVDK   420
SRWQQGNVFS CSVMHEALHN HYTQKSLSLS PG                                452

SEQ ID NO: 6               moltype = AA   length = 214
FEATURE                    Location/Qualifiers
source                     1..214
                           mol_type = protein
                           organism = synthetic construct
SEQUENCE: 6
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNSYPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 7               moltype = AA   length = 5
FEATURE                    Location/Qualifiers
source                     1..5
                           mol_type = protein
                           organism = synthetic construct
SEQUENCE: 7
SYAFS                                                                5

SEQ ID NO: 8               moltype = AA   length = 6
FEATURE                    Location/Qualifiers
source                     1..6
                           mol_type = protein
                           organism = synthetic construct
SEQUENCE: 8
PQLGIA                                                               6

SEQ ID NO: 9               moltype = AA   length = 9
FEATURE                    Location/Qualifiers
source                     1..9
                           mol_type = protein
                           organism = synthetic construct
SEQUENCE: 9
DIAALGPFD                                                            9

SEQ ID NO: 10              moltype = AA   length = 5
```

```
FEATURE             Location/Qualifiers
source              1..5
                    mol_type = protein
                    organism = synthetic construct
SEQUENCE: 10
SYTIN                                                                            5

SEQ ID NO: 11       moltype = AA  length = 4
FEATURE             Location/Qualifiers
source              1..4
                    mol_type = protein
                    organism = synthetic construct
SEQUENCE: 11
PIFG                                                                             4

SEQ ID NO: 12       moltype = AA  length = 12
FEATURE             Location/Qualifiers
source              1..12
                    mol_type = protein
                    organism = synthetic construct
SEQUENCE: 12
SGGSADYSYG MD                                                                   12

SEQ ID NO: 13       moltype = AA  length = 7
FEATURE             Location/Qualifiers
source              1..7
                    mol_type = protein
                    organism = synthetic construct
SEQUENCE: 13
SQGISSW                                                                          7

SEQ ID NO: 14       moltype =   length =
SEQUENCE: 14
000

SEQ ID NO: 15       moltype = AA  length = 6
FEATURE             Location/Qualifiers
source              1..6
                    mol_type = protein
                    organism = synthetic construct
SEQUENCE: 15
YNSYPR                                                                           6

SEQ ID NO: 16       moltype = AA  length = 6
FEATURE             Location/Qualifiers
source              1..6
                    mol_type = protein
                    organism = synthetic construct
SEQUENCE: 16
PFLGIA                                                                           6

SEQ ID NO: 17       moltype = AA  length = 6
FEATURE             Location/Qualifiers
source              1..6
                    mol_type = protein
                    organism = synthetic construct
SEQUENCE: 17
PHLGIA                                                                           6

SEQ ID NO: 18       moltype = AA  length = 6
FEATURE             Location/Qualifiers
source              1..6
                    mol_type = protein
                    organism = synthetic construct
SEQUENCE: 18
PFLGTA                                                                           6

SEQ ID NO: 19       moltype = AA  length = 17
FEATURE             Location/Qualifiers
source              1..17
                    mol_type = protein
                    organism = synthetic construct
SEQUENCE: 19
AAEPKSSDKT HTCPPCP                                                              17

SEQ ID NO: 20       moltype = AA  length = 4
FEATURE             Location/Qualifiers
source              1..4
                    mol_type = protein
```

```
                        organism = synthetic construct
SEQUENCE: 20
GGGG                                                                            4

SEQ ID NO: 21           moltype = AA  length = 14
FEATURE                 Location/Qualifiers
source                  1..14
                        mol_type = protein
                        organism = synthetic construct
SEQUENCE: 21
GGGGDKTHTC PPCP                                                                14

SEQ ID NO: 22           moltype = AA  length = 5
FEATURE                 Location/Qualifiers
source                  1..5
                        mol_type = protein
                        organism = synthetic construct
SEQUENCE: 22
GSGGS                                                                           5

SEQ ID NO: 23           moltype = AA  length = 5
FEATURE                 Location/Qualifiers
source                  1..5
                        mol_type = protein
                        organism = synthetic construct
SEQUENCE: 23
GGGGS                                                                           5

SEQ ID NO: 24           moltype = AA  length = 4
FEATURE                 Location/Qualifiers
source                  1..4
                        mol_type = protein
                        organism = synthetic construct
SEQUENCE: 24
GGGS                                                                            4
```

What is claimed is:

1. A common light chain bispecific antibody comprising:
   (i) an anti-CD38 heavy chain variable region, an anti-CD38 heavy chain constant region, and a first common light chain variable region, wherein:
      the anti-CD38 heavy chain variable region comprises:
      a heavy chain complementarity determining region 1 (HCDR1) comprising an amino acid sequence set forth in SEQ ID NO: 7,
      a heavy chain complementarity determining region 2 (HCDR2) comprising an amino acid sequence set forth in SEQ ID NO: 8,
      a heavy chain complementarity determining region 3 (HCDR3) comprising an amino acid sequence set forth in SEQ ID NO: 9, and
      a negatively-charged amino acid at heavy chain variable region position 1 per Kabat numbering, and
      the first common light chain variable region comprises:
      a light chain complementarity determining region 1 (LCDR1) comprising an amino acid sequence set forth in SEQ ID NO: 13,
      a light chain complementarity determining region 2 (LCDR2) comprising the amino acid sequence AAS, and
      a light chain complementarity determining region 3 (LCDR3) comprising an amino acid sequence set forth in SEQ ID NO: 15; and
   (ii) an anti-CD 19 heavy chain variable region, an anti-CD 19 heavy chain constant region, and a second common light chain variable region, wherein:
      the anti-human-CD 19 heavy chain variable region comprises:
      a heavy chain complementarity determining region 1 (HCDR1) comprising an amino acid sequence set forth in SEQ ID NO: 10,
      a heavy chain complementarity determining region 2 (HCDR2) comprising an amino acid sequence set forth in SEQ ID NO: 11,
      a heavy chain complementarity determining region 3 (HCDR3) comprising an amino acid sequence set forth in SEQ ID NO: 12, and
      a negatively-charged amino acid at heavy chain variable region position 1 per Kabat numbering, and
      the second common light chain variable region comprises:
      a light chain complementarity determining region 1 (LCDR1) comprising an amino acid sequence set forth in SEQ ID NO: 13,
      a light chain complementarity determining region 2 (LCDR2) comprising the amino acid sequence AAS, and
      a light chain complementarity determining region 3 (LCDR3) comprising an amino acid sequence set forth in SEQ ID NO: 15,
   wherein:
      the anti-CD38 heavy chain constant region and the anti-CD19 heavy chain constant region each lack a C-terminal lysine residue; and
      the common light chain bispecific antibody comprises an experimental isoelectric point (pI) of less than 9.0; and
      the first common light chain variable region and the second common light chain variable region comprise an identical amino acid sequence.

2. The common light chain bispecific antibody of claim 1, wherein the common light chain bispecific antibody further comprises a first common light chain constant region and a second common light chain constant region, and:

(i) the anti-CD38 heavy chain variable region and the anti-CD38 heavy chain constant region comprise the amino acid sequence of SEQ ID NO: 4;
(ii) the anti-CD19 heavy chain variable region and the anti-CD19 heavy chain constant region comprise the amino acid sequence of SEQ ID NO: 5; and
(iii) the first common light chain variable region and the first common light chain constant region comprise the amino acid sequence of SEQ ID NO: 6; and
(iv) the second common light chain variable region and the second common light chain constant region comprise the amino acid sequence of SEQ ID NO: 6.

3. The common light chain bispecific antibody of claim 1, wherein the common light chain bispecific antibody further comprises a Hydrophobicity Interaction Chromatography (HIC) retention time of less than about 10 minutes.

4. The common light chain bispecific antibody of claim 1, wherein the terminal lysine residue is K447 per EU numbering.

5. The common light chain bispecific antibody of claim 1, wherein the anti-CD19 heavy chain variable region comprises a serine at position 84 and/or a leucine at position 108 per Kabat numbering.

6. The common light chain bispecific antibody of claim 1, wherein the common light chain variable region comprises a histidine at position 32 per Kabat numbering.

7. The common light chain bispecific antibody of claim 1, wherein the negatively-charged amino acid is glutamic acid.

8. The common light chain bispecific antibody of claim 1, wherein the pI is between 8.7 and 9.0.

9. The common light chain bispecific antibody of claim 1, wherein the anti-CD19 heavy chain constant region comprises a T366W substitution per EU numbering or T366S/L368A/Y407V substitution per EU numbering.

10. The common light chain bispecific antibody of claim 1, wherein the anti-CD38 heavy chain constant region comprises a T366W substitution per EU numbering or T366S/L368A/Y407V substitution per EU numbering.

11. A composition comprising one or more nucleic acid molecules encoding the common light chain bispecific antibody of claim 1.

12. A cell comprising one or more nucleic acid molecules encoding the common light chain bispecific antibody of claim 2.

13. A method of reducing an experimental isoelectric point of an antibody, the method comprising:
(a) mutating a glutamine to a negatively charge amino acid at position 1 of a heavy chain variable region per Kabat numbering; and
(b) removing a lysine at the C-terminal position of a heavy chain constant region, wherein the antibody is a common light chain bispecific antibody comprising:

(i) an anti-CD38 heavy chain variable region, an anti-CD38 heavy chain constant region, and a first common light chain variable region, wherein:
the anti-CD38 heavy chain variable region comprises:
a heavy chain complementarity determining region 1 (HCDR1) comprising an amino acid sequence set forth in SEQ ID NO: 7,
a heavy chain complementarity determining region 2 (HCDR2) comprising an amino acid sequence set forth in SEQ ID NO: 8,
a heavy chain complementarity determining region 3 (HCDR3) comprising an amino acid sequence set forth in SEQ ID NO: 9, and
the negatively-charged amino acid in the heavy chain variable region at position 1 per Kabat numbering, and
the first common light chain variable region comprises:
a light chain complementarity determining region 1 (LCDR1) comprising an amino acid sequence set forth in SEQ ID NO: 13,
a light chain complementarity determining region 2 (LCDR2) comprising the amino acid sequence AAS, and
a light chain complementarity determining region 3 (LCDR3) comprising an amino acid sequence set forth in SEQ ID NO: 15; and
(ii) an anti-CD 19 heavy chain variable region, an anti-CD 19 heavy chain constant region, and a second common light chain variable region, wherein:
the anti-human-CD 19 heavy chain variable region comprises:
a heavy chain complementarity determining region 1 (HCDR1) comprising an amino acid sequence set forth in SEQ ID NO: 10,
a heavy chain complementarity determining region 2 (HCDR2) comprising an amino acid sequence set forth in SEQ ID NO: 11,
a heavy chain complementarity determining region 3 (HCDR3) comprising an amino acid sequence set forth in SEQ ID NO: 12, and
the negatively-charged amino acid in the heavy chain variable region at position 1 per Kabat numbering, and
the second common light chain variable region comprises:
a light chain complementarity determining region 1 (LCDR1) comprising an amino acid sequence set forth in SEQ ID NO: 13,
a light chain complementarity determining region 2 (LCDR2) comprising the amino acid sequence AAS, and
a light chain complementarity determining region 3 (LCDR3) comprising an amino acid sequence set forth in SEQ ID NO: 15.

* * * * *